US012569290B2

(12) United States Patent
Norton et al.

(10) Patent No.: US 12,569,290 B2
(45) Date of Patent: Mar. 10, 2026

(54) SURGICAL ABLATION TOOLS AND METHODS FOR USING THE SAME

(71) Applicant: Medtronic, Inc., Minneapolis, MN (US)

(72) Inventors: Jeffrey A. Norton, Redwood City, CA (US); Calin Druma, San Jose, CA (US); Robert C. Gutierrez, San Ramon, CA (US)

(73) Assignee: Medtronic, Inc., Minneapolis, MN (US)

( * ) Notice: Subject to any disclaimer, the term of this patent is extended or adjusted under 35 U.S.C. 154(b) by 414 days.

(21) Appl. No.: 18/153,614

(22) Filed: Jan. 12, 2023

(65) Prior Publication Data

US 2023/0255679 A1     Aug. 17, 2023

Related U.S. Application Data

(60) Provisional application No. 63/309,890, filed on Feb. 14, 2022.

(51) Int. Cl.
*A61B 18/14* (2006.01)
*A61B 18/00* (2006.01)

(52) U.S. Cl.
CPC .... *A61B 18/14* (2013.01); *A61B 2018/00083* (2013.01); *A61B 2018/00577* (2013.01); *A61B 2018/00821* (2013.01); *A61B 2018/1432* (2013.01)

(58) Field of Classification Search
CPC .......... A61B 18/00; A61B 2018/00053; A61B 2018/1405; A61B 18/1482; A61B 18/00339; A61B 18/14

USPC ......................................................... 606/41
See application file for complete search history.

(56) References Cited

U.S. PATENT DOCUMENTS

| | | | |
|---|---|---|---|
| 5,486,161 A | 1/1996 | Lax et al. | |
| 6,162,216 A | 12/2000 | Guziak et al. | |
| 7,037,290 B2 | 5/2006 | Gardeski et al. | |
| 10,111,704 B2 | 10/2018 | Pellegrino | |
| 12,076,074 B2 * | 9/2024 | Godara | A61B 18/1402 |
| 2006/0178666 A1 | 8/2006 | Cosman et al. | |
| 2008/0275483 A1 | 11/2008 | Makower et al. | |
| 2015/0297246 A1 | 10/2015 | Patel et al. | |
| 2018/0147007 A1 * | 5/2018 | Purdy | A61B 18/10 |
| 2019/0076179 A1 | 3/2019 | Babkin et al. | |
| 2020/0146744 A1 * | 5/2020 | Defosset | A61B 18/148 |

OTHER PUBLICATIONS

International Search Report and Written Opinion for International (PCT) Patent Application No. PCT/IB2023/050873, dated Jun. 16, 2023, 20 pages.

* cited by examiner

*Primary Examiner* — Beverly M Flanagan
(74) *Attorney, Agent, or Firm* — Sheridan Ross P.C.

(57) ABSTRACT

A surgical tool for ablating anatomical tissue according to at least one embodiment of the present disclosure includes: a distal tip; a first cylindrical tube connected to the distal tip; a second cylindrical tube that at least partially overlaps the first cylindrical tube in a first direction; and a J-shaped stylet disposed in an interior of the surgical tool, the J-shaped stylet capable of being removed from the interior of the surgical tool.

20 Claims, 24 Drawing Sheets

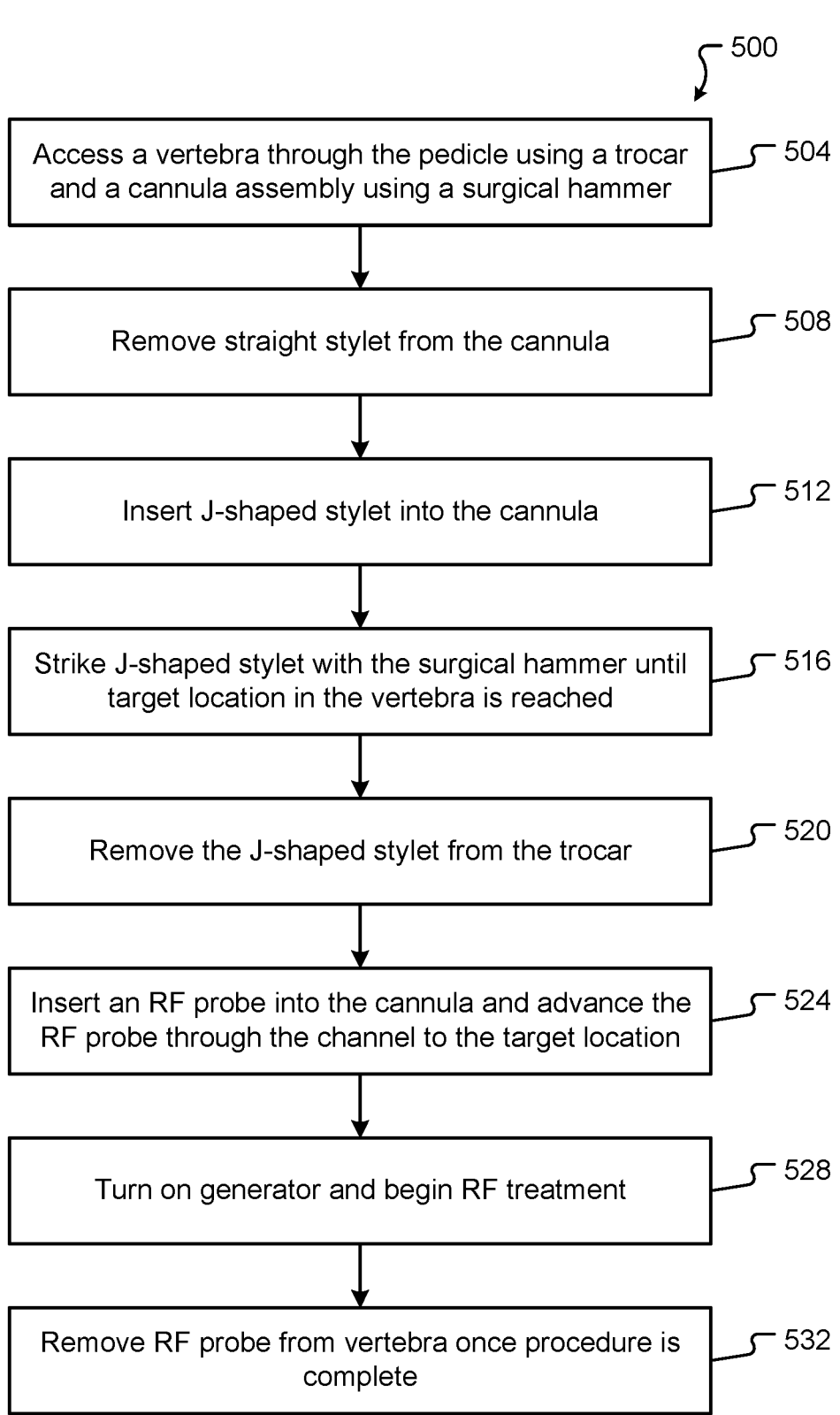

500

Access a vertebra through the pedicle using a trocar and a cannula assembly using a surgical hammer — 504

Remove straight stylet from the cannula — 508

Insert J-shaped stylet into the cannula — 512

Strike J-shaped stylet with the surgical hammer until target location in the vertebra is reached — 516

Remove the J-shaped stylet from the trocar — 520

Insert an RF probe into the cannula and advance the RF probe through the channel to the target location — 524

Turn on generator and begin RF treatment — 528

Remove RF probe from vertebra once procedure is complete — 532

FIG. 5

SURGICAL ABLATION TOOLS AND METHODS FOR USING THE SAME

CROSS-REFERENCE TO RELATED APPLICATIONS

The present application claims the benefit of and priority to U.S. Provisional Application No. 63/309,890, filed on Feb. 14, 2022, entitled "SURGICAL ABLATION TOOLS AND METHODS FOR USING THE SAME", which application is incorporated herein by reference in its entirety.

BACKGROUND

The present disclosure is generally directed to surgical tools, and relates more particularly to surgical tools capable of ablating anatomical tissue.

Surgical robots may assist a surgeon or other medical provider in carrying out a surgical procedure, or may complete one or more surgical procedures autonomously. Providing controllable linked articulating members allows a surgical robot to reach areas of a patient anatomy during various medical procedures.

BRIEF SUMMARY

Example aspects of the present disclosure include:

A surgical tool for ablating anatomical tissue according to at least one embodiment of the present disclosure comprises: a distal tip; a first cylindrical tube connected to the distal tip; a second cylindrical tube that at least partially overlaps the first cylindrical tube in a first direction; and a J-shaped stylet disposed in an interior of the surgical tool, the J-shaped stylet configured to be removed from the interior of the surgical tool.

Any of the aspects herein, further comprising: a first insulative layer disposed between and electrically isolating the first cylindrical tube and the second cylindrical tube; and a heat shrinkable layer disposed around at least a portion of the second cylindrical tube.

Any of the aspects herein, wherein the J-shaped stylet is connected to a pull handle, and wherein the pull handle is configured to be pulled to extract the J-shaped stylet from the interior of the surgical tool.

Any of the aspects herein, wherein the distal tip comprises a hole, and wherein a portion of the J-shaped stylet extends through the hole of the distal tip.

Any of the aspects herein, further comprising: a thermocouple disposed in the interior of the surgical tool and contacting the distal tip, the thermocouple configured to generate a reading of a temperature of the distal tip.

Any of the aspects herein, wherein at least one of the first cylindrical tube or the second cylindrical tube is segmented or braided.

Any of the aspects herein, further comprising: a cannula handle; and a cannula tube connected to the cannula handle, wherein a portion of at least one of the first cylindrical tube, the second cylindrical tube, and the first insulative layer is positioned in an interior of the cannula tube.

Any of the aspects herein, wherein at least one of the first cylindrical tube and the second cylindrical tube comprises stainless steel.

Any of the aspects herein, wherein the J-shaped stylet comprises Nitinol.

Any of the aspects herein, wherein a Radiofrequency (RF) current flows from the first cylindrical tube to the anatomical tissue and from the anatomical tissue into the second cylindrical tube.

A surgical tool according to at least one embodiment of the present disclosure comprises: a first conductive tube extending from a proximal end of the surgical tool to a distal end of the surgical tool, the first conductive tube configured to pass a current into an anatomical tissue; a second conductive tube extending from the proximal end of the surgical tool to a first distance from the distal end of the surgical tool, the second conductive tube configured to receive the current passing through the anatomical tissue; and a ceramic tip attached to a distal end of the first conductive tube.

Any of the aspects herein, further comprising: a first insulation layer disposed between the first conductive tube and the second conductive tube that electrically isolates the first conductive tube from the second conductive tube; and a heat shrinkable material disposed around at least a portion of the second conductive tube.

Any of the aspects herein, further comprising: a metal core disposed within the first conductive tube, the metal core mechanically coupled with the ceramic tip.

Any of the aspects herein, wherein a plurality of interlocking keys mechanically couples the metal core with the ceramic tip.

Any of the aspects herein, further comprising: a thermocouple connected to the first conductive tube, the thermocouple configured to generate a measurement of a temperature of the first conductive tube.

Any of the aspects herein, wherein the ceramic tip is thermally and electrically insulative.

Any of the aspects herein, further comprising: a cannula handle; a clamshell disposed proximal to the cannula handle; and a dial indicator disposed proximal to the clamshell, the dial indicator mechanically coupled with the metal core.

Any of the aspects herein, further comprising: a strike zone disposed at least partially within the dial indicator and attached to the metal core.

Any of the aspects herein, further comprising: a second insulation layer disposed between the first conductive tube and the metal core that electrically isolates at least one of the ceramic tip and the metal core from the first conductive tube.

Any of the aspects herein, wherein the metal core comprises Nitinol.

A surgical tool according to at least one embodiment of the present disclosure comprises: a proximal end; a distal end, the distal end including: a first cylindrical electrode; a second cylindrical electrode; a metal core disposed at least partially within the first cylindrical electrode; and a ceramic tip attached to the metal core.

Any of the aspects herein, wherein the proximal end of the surgical tool further comprises: a dial indicator; and a strike zone at least partially embedded in the dial indicator and coupled with the metal core.

Any of the aspects herein, wherein the distal end of the surgical tool further comprises: a first cylindrical insulation layer disposed between the first cylindrical electrode and the second cylindrical electrode.

Any of the aspects herein, wherein the distal end of the surgical tool further comprises: a type k thermocouple disposed within an interior of the first cylindrical electrode and configured to generate a measurement of a temperature of the first cylindrical electrode.

Any of the aspects herein, wherein the dial indicator, when rotated in a first direction, causes the ceramic tip to rotate in the first direction.

Any of the aspects herein, wherein the dial indicator, when rotated in a second direction different from the first direction, causes the ceramic tip to rotate in the second direction.

Any of the aspects herein, wherein the ceramic tip is attached to the metal core with one or more interlocking keys.

Any of the aspects herein, wherein the first cylindrical electrode and the second cylindrical electrode comprise stainless steel.

Any of the aspects herein, wherein the metal core comprises Nitinol.

Any of the aspects herein, wherein the ceramic tip is thermally and electrically insulative.

An apparatus according to at least one embodiment of the present disclosure comprises: a cannula handle; a cannula tube attached to the cannula handle; a surgical tool capable of passing through an interior of the cannula tube to access an anatomical tissue, the surgical tool comprising: a distal electrode; a surgical tip disposed on a distal end of the distal electrode; a proximal electrode; and aa metal core at least partially disposed within the distal electrode and mechanically coupled with the surgical tip.

Any of the aspects herein, further comprising: a strike zone mechanically coupled with the metal core such that, when a first force hits the strike zone, the first force is transferred to the surgical tip.

Any of the aspects herein, wherein the surgical tool further comprises: a first insulation disposed between and electrically isolating the distal electrode and the proximal electrode.

Any of the aspects herein, wherein the surgical tool further comprises: a second insulation disposed around at least a portion of the proximal electrode.

Any of the aspects herein, wherein the surgical tip is electrically insulative.

Any of the aspects herein, wherein the surgical tool further comprises: a thermocouple that contacts the distal electrode and is configured to generate a measurement of a temperature of the distal electrode.

Any of the aspects herein, wherein the surgical tip comprises ceramic.

Any of the aspects herein, wherein the surgical tip is electrically conductive.

Any of the aspects herein, wherein the surgical tool further comprises: a thermocouple that contacts at least one of the distal electrode or the surgical tip, the thermocouple configured to generate a measurement of a temperature of at least one of the distal electrode or the surgical tip.

Any of the aspects herein, wherein the surgical tip comprises Nitinol.

An apparatus according to at least one embodiment of the present disclosure comprises: a J-shaped stylet; and a Radiofrequency (RF) probe, the RF probe comprising: a first electrode extending from a proximal end of the RF probe to a distal end of the RF probe; a second electrode extending from the proximal end of the RF probe to a first distance from the distal end of the RF probe; and a conductive tip electrically coupled with the first electrode, wherein the J-shaped stylet is disposed in an interior portion of the RF probe and configured to be extracted from the interior portion through the proximal end of the RF probe.

Any of the aspects herein, wherein the RF probe further comprises: a first insulation layer disposed around the first electrode, the first insulation layer electrically isolating the first electrode and the second electrode.

Any of the aspects herein, wherein the J-shaped stylet further comprises: a metal core attached to the J-shaped stylet; and a pull handle attached to the metal core, wherein the pull handle, when pulled toward the proximal end of the RF probe, causes the metal core and the J-shaped stylet to slide out of the interior portion of the RF probe.

Any of the aspects herein, wherein the RF probe further comprises: a heat shrinkable material disposed around at least a portion of the second electrode.

Any of the aspects herein, wherein the RF probe further comprises: a thermocouple coupled with the conductive tip, the thermocouple configured to generate a reading indicative of a temperature of the conductive tip.

Any of the aspects herein, wherein the apparatus further comprises: a cannula handle; and a cannula tube extending from the cannula handle in a first direction, wherein the RF probe is at least partially contained within the cannula tube.

Any of the aspects herein, wherein at least one of the metal core or the J-shaped stylet comprises Nitinol.

Any of the aspects herein, wherein the heat shrinkable material comprises polyethylene terephthalate, polyether ether ketone, or polyimide.

Any of the aspects herein, wherein the first electrode comprises a first cylindrical tube, wherein the second electrode comprises a second cylindrical tube, and wherein a portion of at least one of the metal core or the J-shaped stylet is positioned within the first cylindrical tube.

Any of the aspects herein, wherein the second cylindrical tube at least partially overlaps the first cylindrical tube in a first direction.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 5 is a flowchart according to at least one embodiment of the present disclosure.

DETAILED DESCRIPTION

Figure 1A:
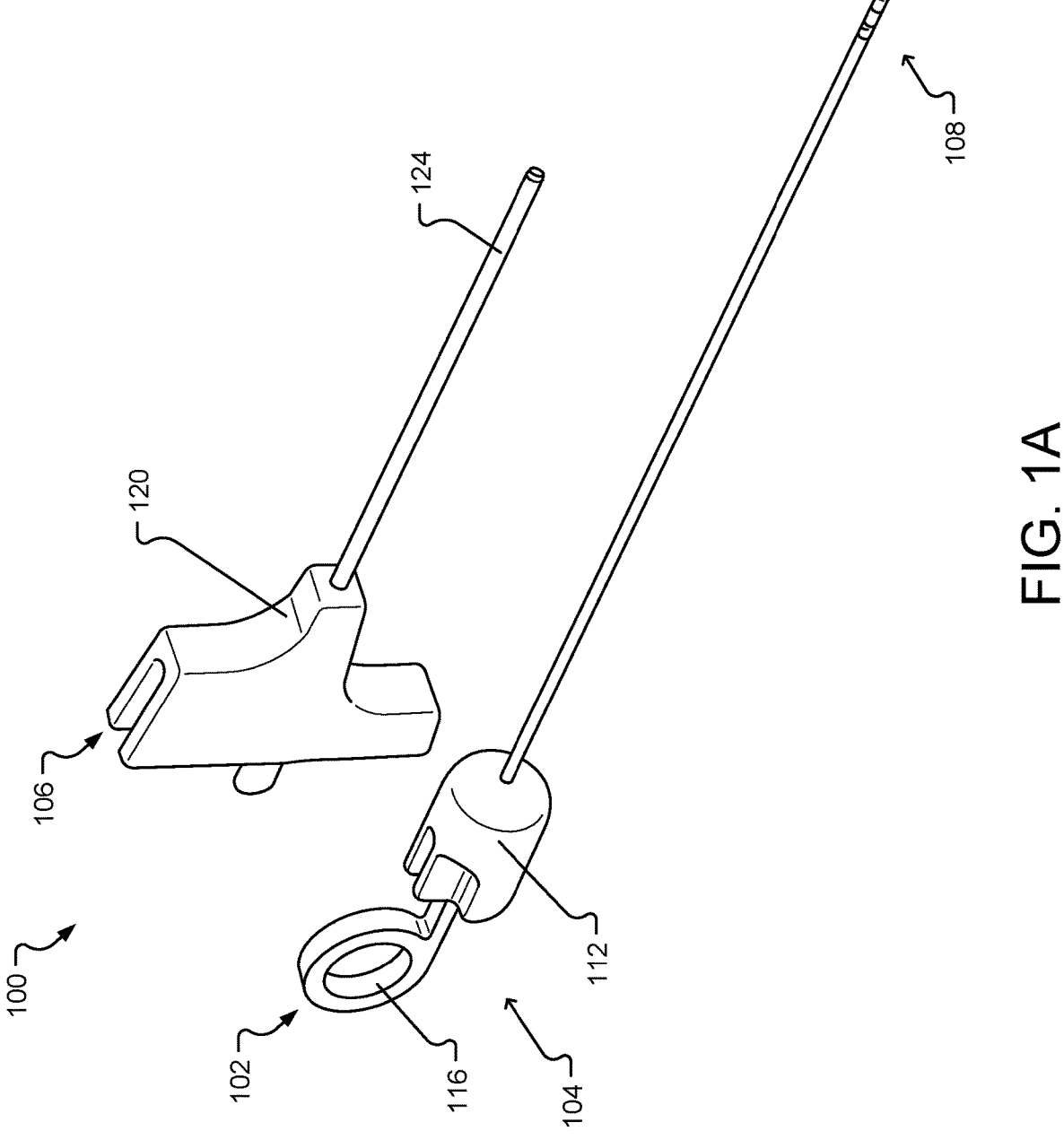
FIG. 1A is an isometric view of components of a surgical assembly according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia Geforce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Lumbar axial back pain arising from degenerative disc disease may present clinical problems, regardless of whether the disease is treated with nonsurgical management, local injection(s), or motion segment stabilization and fusion. The basivertebral nerve (BVN) is a nerve located within a vertebra and is a nerve responsible for the innervation of end plates and nutrient supply for discs above and below the instant vertebral body. Compared with the density of nociceptors in normal endplate regions or in painful degenerated discs, BVN density is much higher in endplate regions with damage, linking these nerves to chronic lower back pain (CLBP). As the disc and endplates degenerate, the communication between the bone marrow and the disc increases due to the hydraulic disc/vertebra coupling and increased convective flow included by cyclic spinal loading. The crosstalk that develops between the disc and bone marrow results in the release of inflammatory mediators. The persisting stimulus sets up a frustrated healing response, leading to an escalating inflammatory response in some individuals and the appearance of Modic changes (MCs) at the vertebral endplates. This inflammatory response is sensed by the BVN and transmitted to the central nervous system, then perceived as lower back pain (LBP).

Radiofrequency (RF) ablation is an interventional method of treatment to destroy the BVN root with RF energy and inhibit the pain transmitted by the BVN to the central nervous system. Patients treated with RF ablation of the BVN for CLBP may exhibit sustained clinical benefits in ODI (Oswestry Disability Index) and VAS (visual analog scale) and may maintain higher responder rates at two years following treatment. BVN ablation thus appears to be a durable, minimally invasive treatment for the relief of CLBP.

According to at least one embodiment of the present disclosure, systems and methods may be used to access the BVN root effectively and destroy the nerve using a bipolar RF probe.

According to at least one embodiment of the present disclosure, the RF probe may include a removable J-shaped stylet made of a Nickle Titanium (Nitinol) alloy that resides in the inner diameter of the RF probe. The J-shaped stylet may provide the otherwise flexible probe shaft its J shape when assembled. Once the stylet is removed after full insertion of the RF probe into the vertebra/target location, the RF probe is easier to remove from the vertebra/target location once the ablation procedure has been completed. The removed J-shaped stylet also reduces the thermal mass of the RF probe, enabling the RF probe to heat the target location faster and more efficiently. The active and/or return electrode may be or comprise segmented stainless steel tubing that limits the heat transfer to other components of the RF probe, while the surface area contacting the anatomical tissue to be ablated is able to heat faster and/or more effectively. Additionally, the segmentation of the stainless steel electrodes may enable the RF probe to deflect in a plurality of directions, such as when the J-shaped stylet is installed within the RF probe.

According to at least one embodiment of the present disclosure, the stainless steel tubes may not be segmented, but may alternatively be a braided wire and/or polymer. The braided wire and/or polymer may be fluid tight and capable of conducting the RF current. Additionally or alternatively, the J-shaped stylet may not be removable from the RF probe, and may be or comprise a hollow tube in a J-shaped configuration. In such embodiments, a coolant (e.g., water, sterilized water, saline, etc.) may be flowed into the hollow tube to the tip of the surgical tool (e.g., the distal electrode) and flowed out of the RF probe in the space between the interior of the electrodes (e.g., the interior diameter of the active electrode and outside the outer diameter of the J-shaped stylet, providing cooling capabilities for the RF probe.

According to at least one embodiment of the present disclosure, an RF probe may include a solid core (e.g., a metal core made of Nitinol material) attached to a hard ceramic tip. The ceramic tip may have low thermal conductivity, and may have the electrodes of the RF probe for performing bipolar ablation disposed proximally thereto. The RF probe may also comprise a memory shape curve that enables medialization of the RF probe to reach the correct location within the vertebral body.

Additionally or alternatively, the ceramic tip may be steerable by, for example, a physician at the proximal end of the RF probe. The steerability may be connected to the metal core (e.g., the Nitinol core) in the innermost layer of the RF probe. For instance, the metal core may be connected to a hammer strike plate that is disposed on the proximal end of the RF probe. As the physician strikes the hammer strike plate, the force generated on the plate may be passed down to the ceramic tip, such that the ceramic tip can cut or bore through the bone to reach the surgical site for ablation.

Embodiments of the present disclosure provide technical solutions to one or more of the problems of (1) using multiple components to access a target surgical site and (2) slow and inefficient ablation of anatomical tissues.

FIGS. 1A-1K depict illustrative features of a surgical assembly 100 in accordance with at least one embodiment of the present disclosure. Turning first to FIG. 1A, an isometric view of the surgical assembly 100 is depicted. The surgical assembly 100 may be used to access a target surgical site and ablate anatomical tissue at the surgical site. The surgical assembly 100 includes a surgical tool 102 and a cannula assembly 106.

Figure 1B:
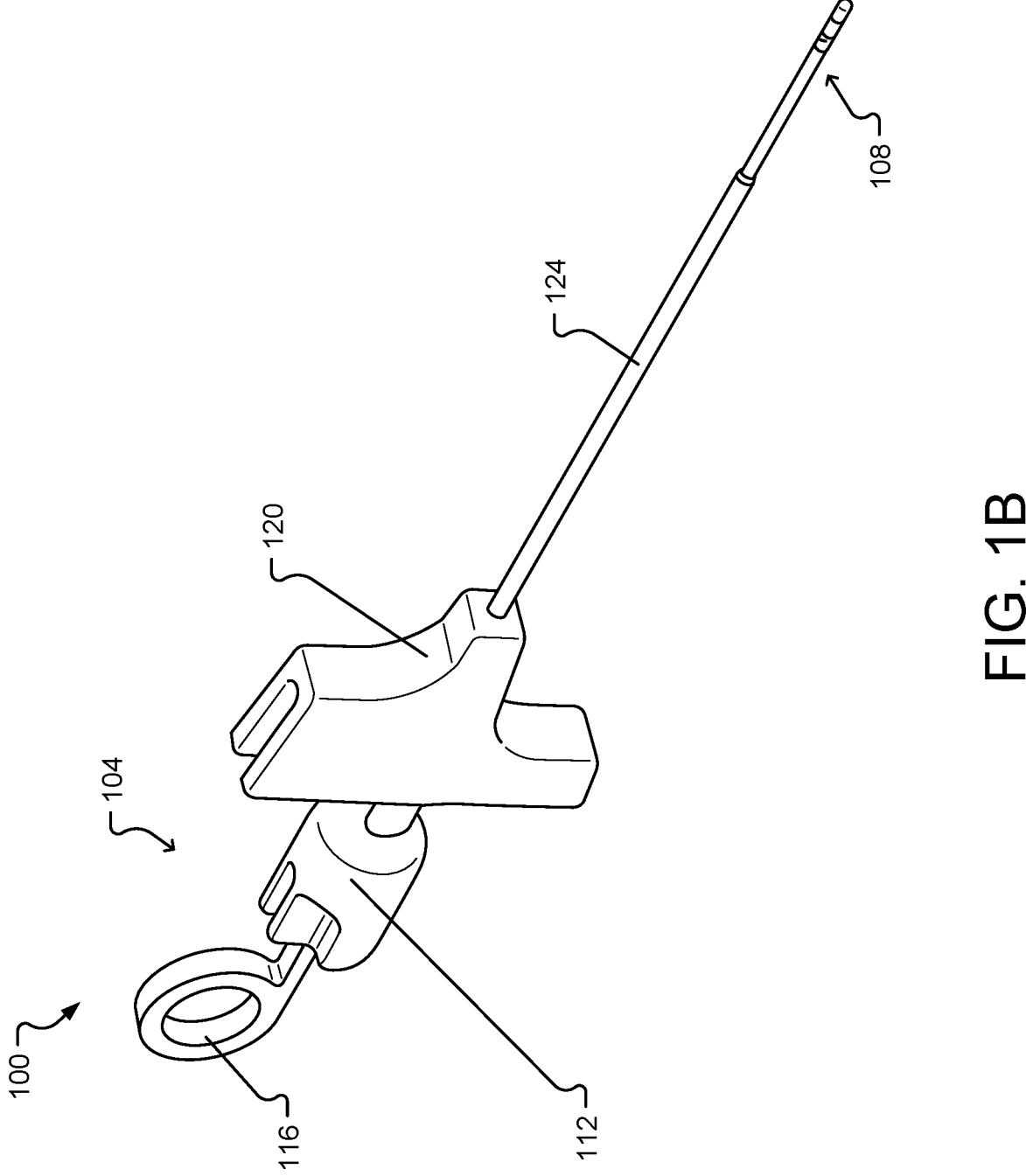
FIG. 1B is an isometric view of a surgical assembly with a surgical tool inserted into a cannula assembly according to at least one embodiment of the present disclosure.

The cannula assembly 106 may comprise tools for accessing the target surgical site and may include a cannula handle 120 and a cannula tube 124. The cannula handle 120 may enable the physician or surgeon to hold the surgical assembly 100 during use. The cannula tube 124 may be a hollow tube attached to a distal end of the cannula handle 120 and may be inserted into a target surgical site (e.g., a vertebra of the patient). In some embodiments, the cannula handle 120 may include a trocar (not shown) that can cut through anatomical tissue to more efficiently reach the surgical site. For instance, to access anatomical tissue within a vertebra, the physician or surgeon may hold the cannula handle 120 and strike (e.g., using a surgical hammer) the top of the cannula handle 120 such that the cannula tube 124 enters (e.g., bores into) the vertebra. In one embodiment, the anatomical tissue within the vertebra may be accessed by hammering through the pedicle of the vertebra. Once the cannula assembly 106 has been used to access the surgical site, the surgical tool 102 may be passed through a hollow portion of the cannula handle 120 and the cannula tube 124 (as shown in FIG. 1B) to permit the surgical tool 102 to access the target surgical site. After the target surgical site has been reached (e.g., the interior of the vertebra) by the surgical tool 102, the ablation components of the surgical tool 102 may be activated to ablate the anatomical tissue at the surgical site.

Figure 1C:
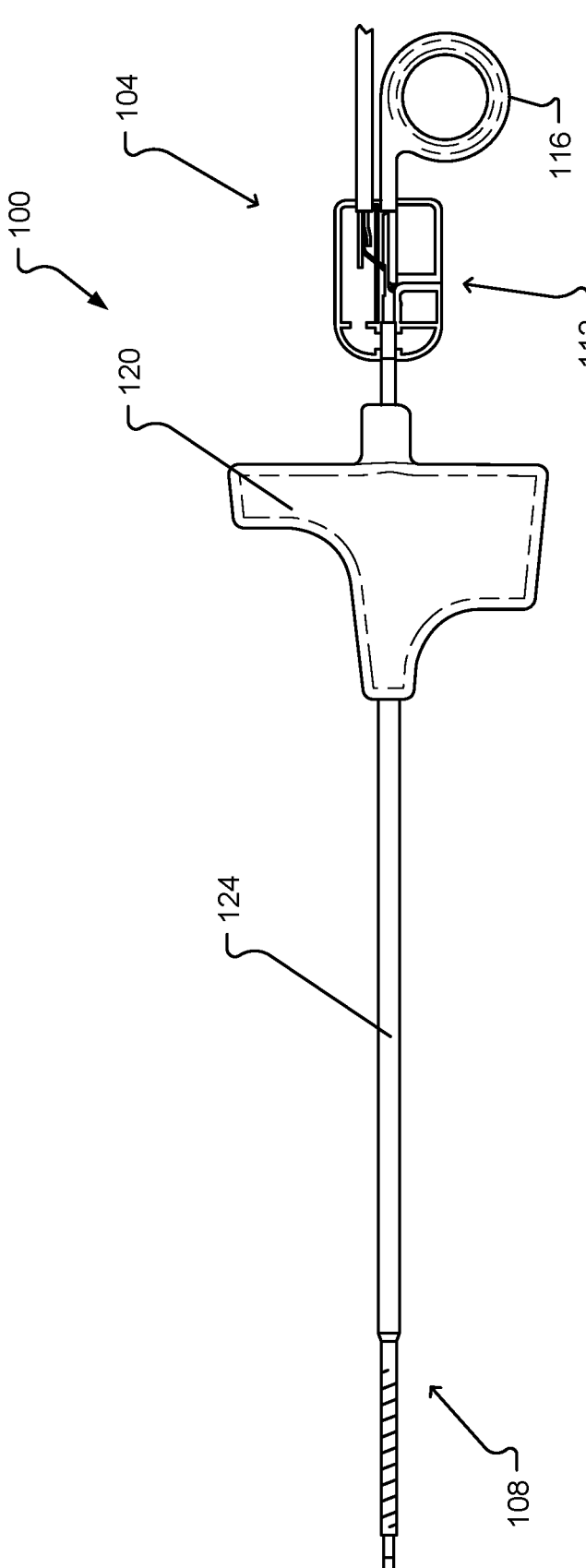
FIG. 1C is a side view of the surgical assembly according to at least one embodiment of the present disclosure.
Figure 1D:
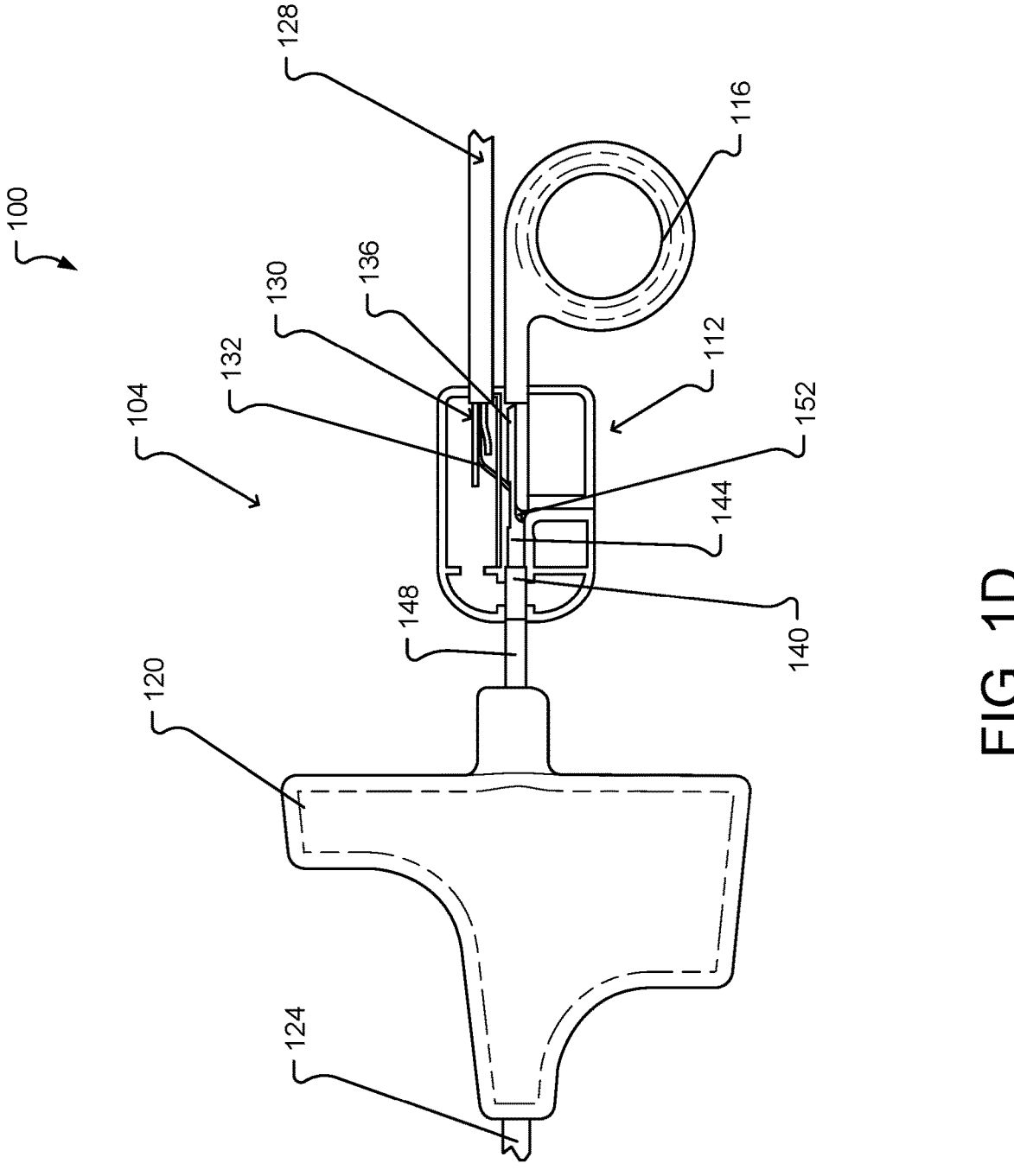
FIG. 1D is a detailed side view of a proximal end of the surgical assembly according to at least one embodiment of the present disclosure.

The surgical tool 102 extends from a proximal end 104 to a distal end 108. The proximal end 104 may be the end of the surgical tool 102 that is positioned closer to the physician and further away from the surgical site, while the distal end 108 may be the end of the surgical tool positioned closer to the surgical site and further away from the physician. The proximal end 104 of the surgical tool 102 may include a clamshell 112 and a pull handle 116. The clamshell 112 may provide a location for the physician to grip the surgical tool 102 during, for example, ablation of the anatomical tissue and may also provide be the location where the electrodes that extend from the proximal end 104 into the distal end 108 connect to an RF generator or other power source. The clamshell 112 may be hollow or otherwise provide a cavity where current-carrying wiring connects to the electrodes of the surgical tool 102. For instance, as shown in FIGS. 1C-1D, the clamshell 112 may contain a port into which a cable 128 may enter. The cable 128 may be an insulative tubing containing wiring 130. The wiring 130 may carry RF current generated by a generator or other power source (not shown) into the surgical tool 102. The cable 128 may also carry or pass a thermocouple 132 into the surgical tool 102.

Figure 1E:
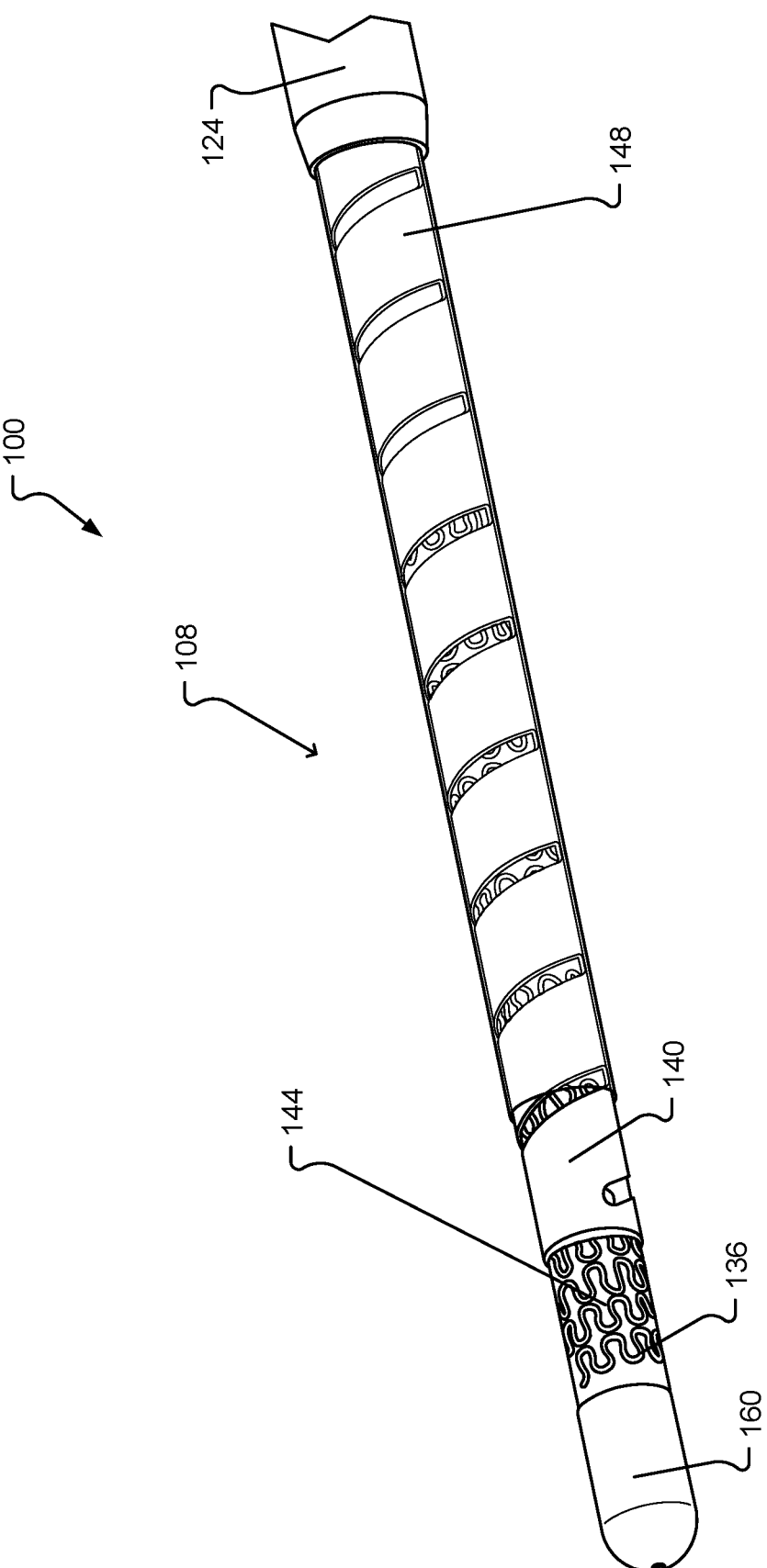
FIG. 1E is a detailed isometric view of a distal end of the surgical assembly according to at least one embodiment of the present disclosure.
Figure 1F:
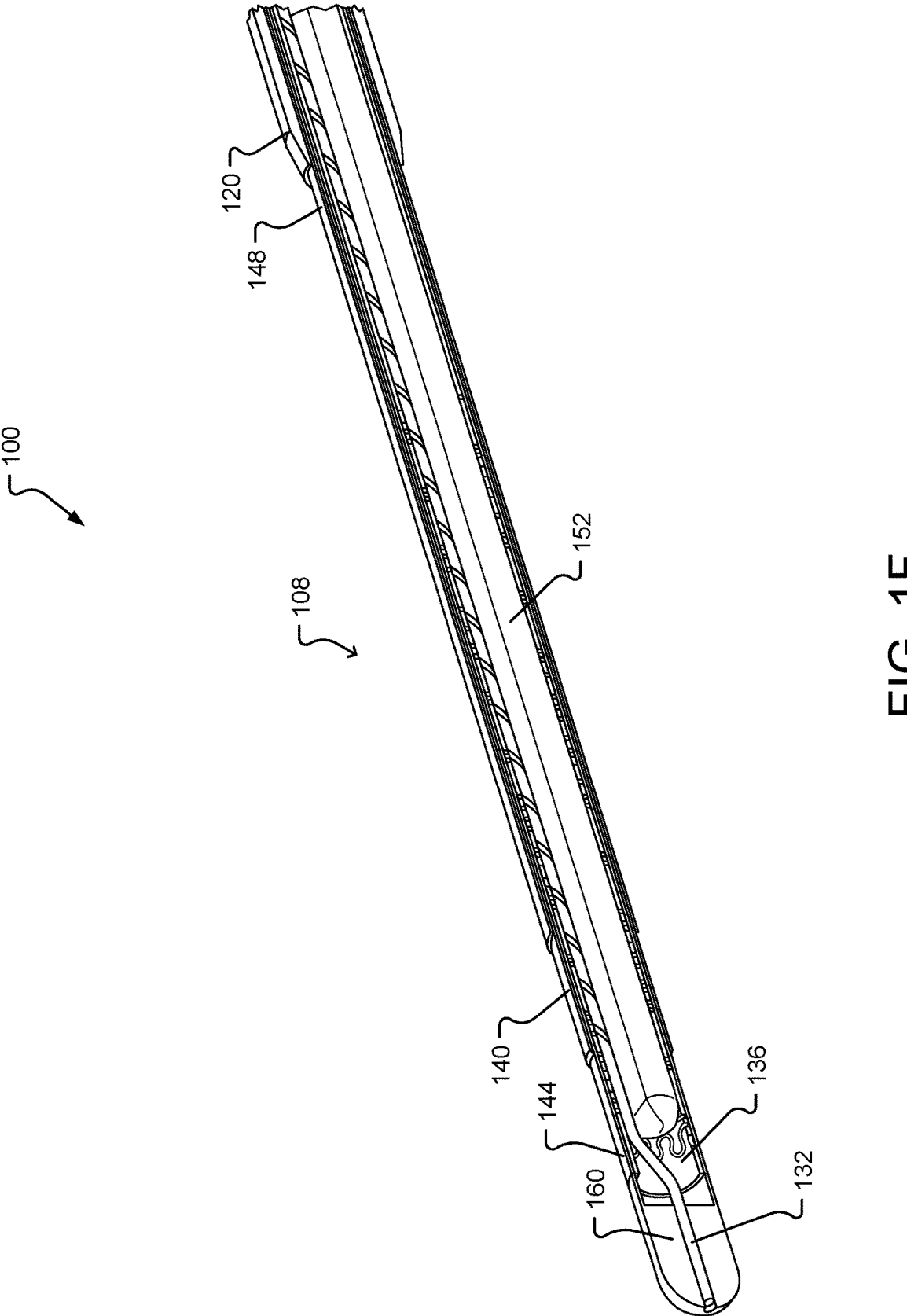
FIG. 1F is a cross section view of the distal end of the surgical assembly according to at least one embodiment of the present disclosure.
Figure 1G:
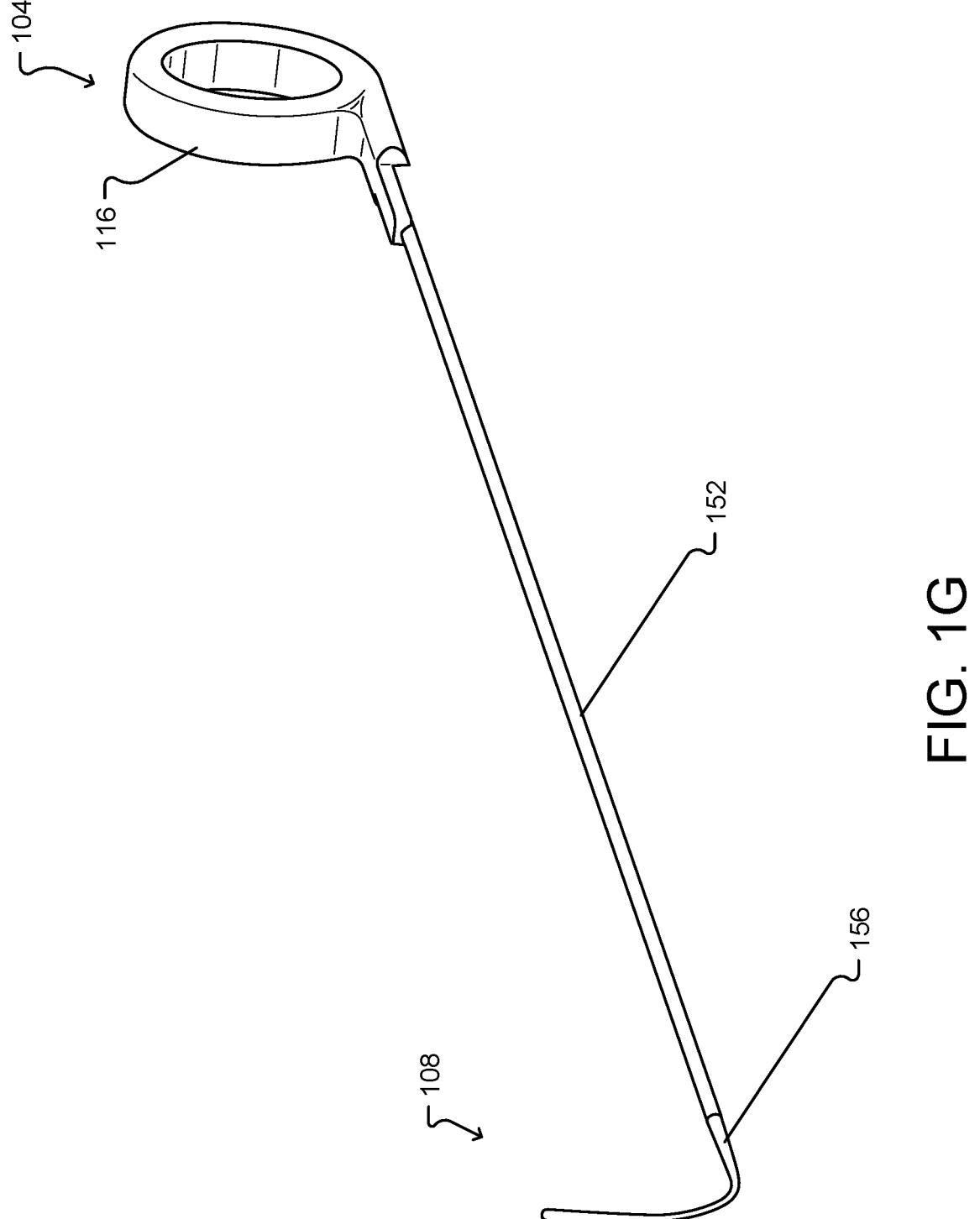
FIG. 1G is an isometric view of components of the surgical assembly according to at least one embodiment of the present disclosure.

The thermocouple 132 may be or comprise one or more sensors that measure the temperature of the electrodes. In some embodiments, each electrode of the surgical tool 102 may be monitored by a separate thermocouple. The sensors may, based on the heating experienced by the electrodes during operation, generate one or more measurements the represent the temperature of the electrodes. In some embodiments, the thermocouple 132 may extend from the cable 128 into the clamshell 112, and may be threaded through or otherwise be disposed in the interior of the surgical tool 102. As illustrated in FIG. 1E, the thermocouple 132 may run along the length of the surgical tool 102 from the proximal end 104 into the distal end 108 to measure the temperature of the electrodes. In some embodiments, the thermocouple 132 may be or comprise a type K thermocouple (e.g., a thermocouple with a temperature range of about 0 degrees Celsius (° C.) to about 1260° C.), a type J thermocouple (e.g., a thermocouple with a temperature range of about 0° C. to about 760° C.), a type N thermocouple (e.g., a thermocouple with a temperature range of about 0° C. to about 1260° C.), a type B thermocouple (e.g., a thermocouple with a temperature range of about 870° C. to about 1700° C.), a type E thermocouple (e.g., a thermocouple with a temperature range of about 0° C. to about 870° C.), a type R thermocouple (e.g., a thermocouple with a temperature range of about 500° C. to about 1500° C.), a type S thermocouple (e.g., a thermocouple with a temperature range of about 500° C. to about 1500° C.), or a type C thermocouple (e.g., a thermocouple with a temperature range of about 0° C. to about 2300° C.). In some embodiments, the surgical assembly 100 may comprise multiple thermocouples to measure the temperature of one or more components (e.g., the electrodes of the surgical tool 102).

The clamshell 112 may also encompass portions of the electrodes of the surgical tool 102 to which the wiring 130 is connected. The surgical tool 102 may include a first electrode 136 and a second electrode 140. As will be discussed further below, the first electrode 136 may be, for example, an active electrode configured to receive an RF current from the wiring 130 (e.g., a first active wire) and carry the RF current to the surgical site at the distal end 108 of the surgical tool 102. The second electrode 140 may be, for example, a return electrode configured to receive the RF current after the RF current has passed through the anatomical tissue at the surgical site and carry the RF current back through the wiring 130 (e.g., a second return wire) to the generator or other power source to complete the circuit. In some embodiments, the surgical tool 102 may also include a first layer of insulation 144 disposed between the first electrode 136 and the second electrode 140, as well as a protective barrier 148 disposed around the second electrode 140. As illustrated in FIG. 1D, the protective barrier 148 may cover the portion of the second electrode 140 disposed outside of the clamshell 112, to help improve safety and provide an insulative layer to prevent or mitigate electric shock in the event that the physician or surgeon contacts the second electrode 140 while the generator or power source is on.

The distal end 108 of the surgical tool 102 may include components that enable RF ablation of anatomical tissue. The distal end 108 may include the first electrode 136, the second electrode 140, the first layer of insulation 144, the protective barrier 148, and a surgical tip 160.

The first electrode 136 and the second electrode 140 may conduct an RF current through proximal anatomical tissue to ablate the anatomical tissue. As previously mentioned, the first electrode 136 may carry the RF current from a generator or other power source into the anatomical tissue, and the second electrode 140 may receive the RF current after the RF current has passed through the anatomical tissue and carry the returning RF current back to the generator or power source. Alternatively, the second electrode 140 may act as the active electrode that carries the RF current into the anatomical tissue, while the first electrode 136 may act as the return electrode that carries the RF current out of the anatomical tissue. In some embodiments, the first electrode 136 may be a distal electrode (e.g., an electrode disposed closer to the patient and/or further away from the physician or surgeon than the proximal electrode) while the second electrode 140 may be a proximal electrode (e.g., an electrode disposed further away from the patient and/or closer to the physician or surgeon than the distal electrode). In such embodiments, the first electrode 136 may be the distal electrode that carries an active RF current from the proximal end 104 of the surgical tool 102 into anatomical tissue, and the second electrode 140 may be the proximal electrode that carries the active RF current out of the anatomical tissue and back toward the proximal end 104 of the surgical tool 102.

Figure 1H:
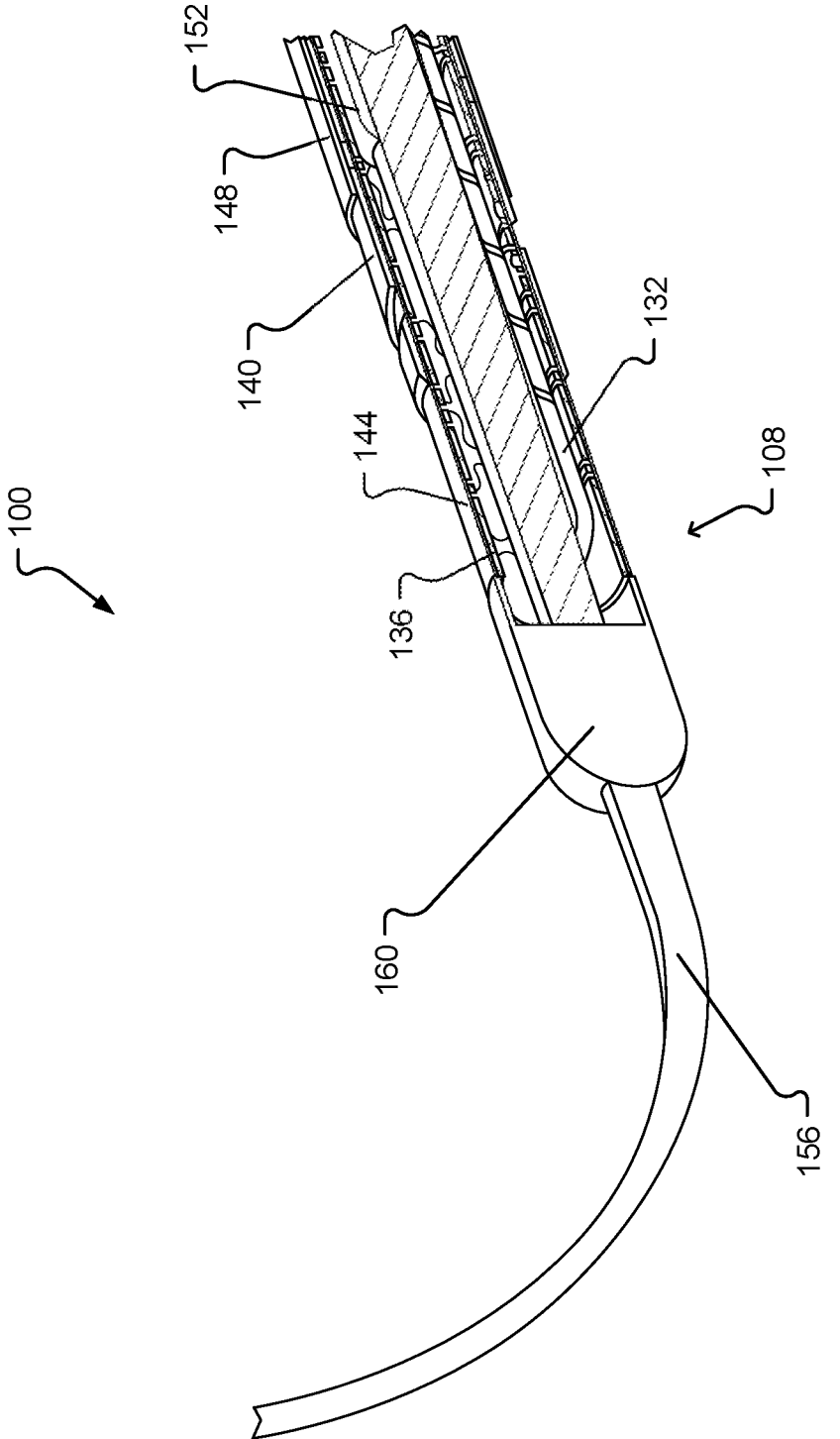
FIG. 1H is an additional cross section view of the distal end of the surgical assembly according to at least one embodiment of the present disclosure.
Figure 1I:
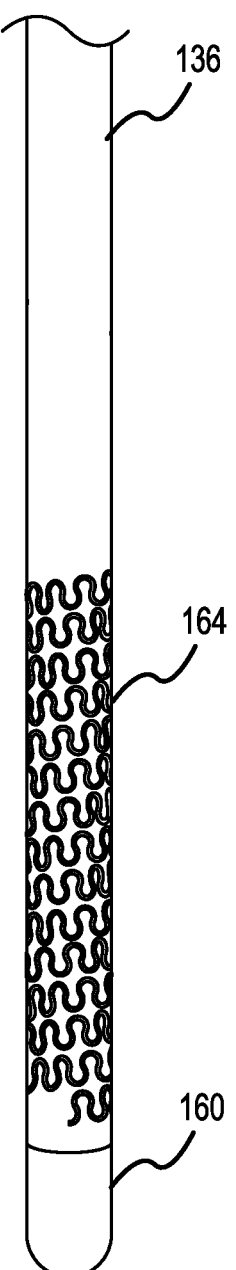
FIG. 1I is a side view of a cylindrical electrode according to at least one embodiment of the present disclosure.
Figure 1J:
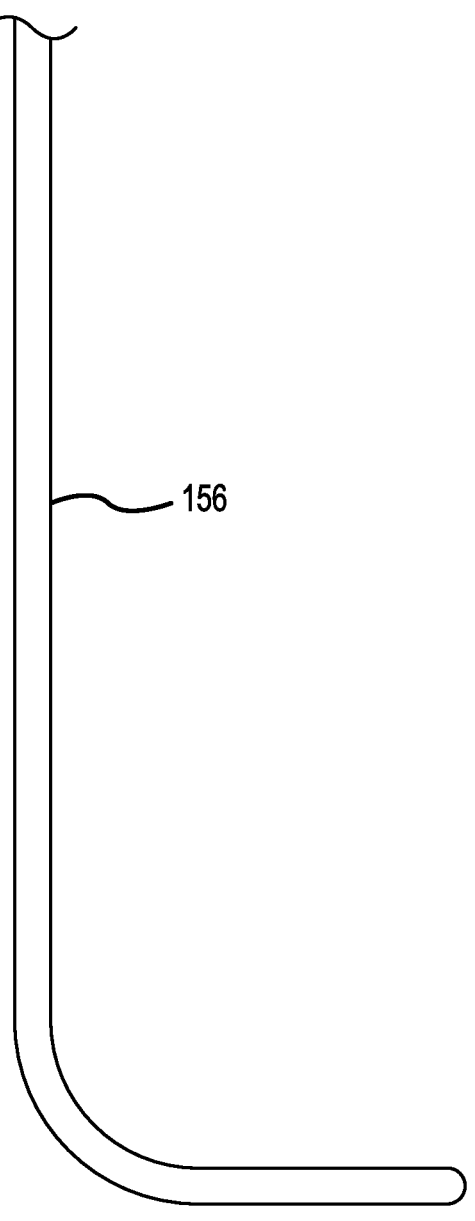
FIG. 1J is a side view of the cylindrical electrode and a J-shaped stylet according to at least one embodiment of the present disclosure.
Figure 1K:
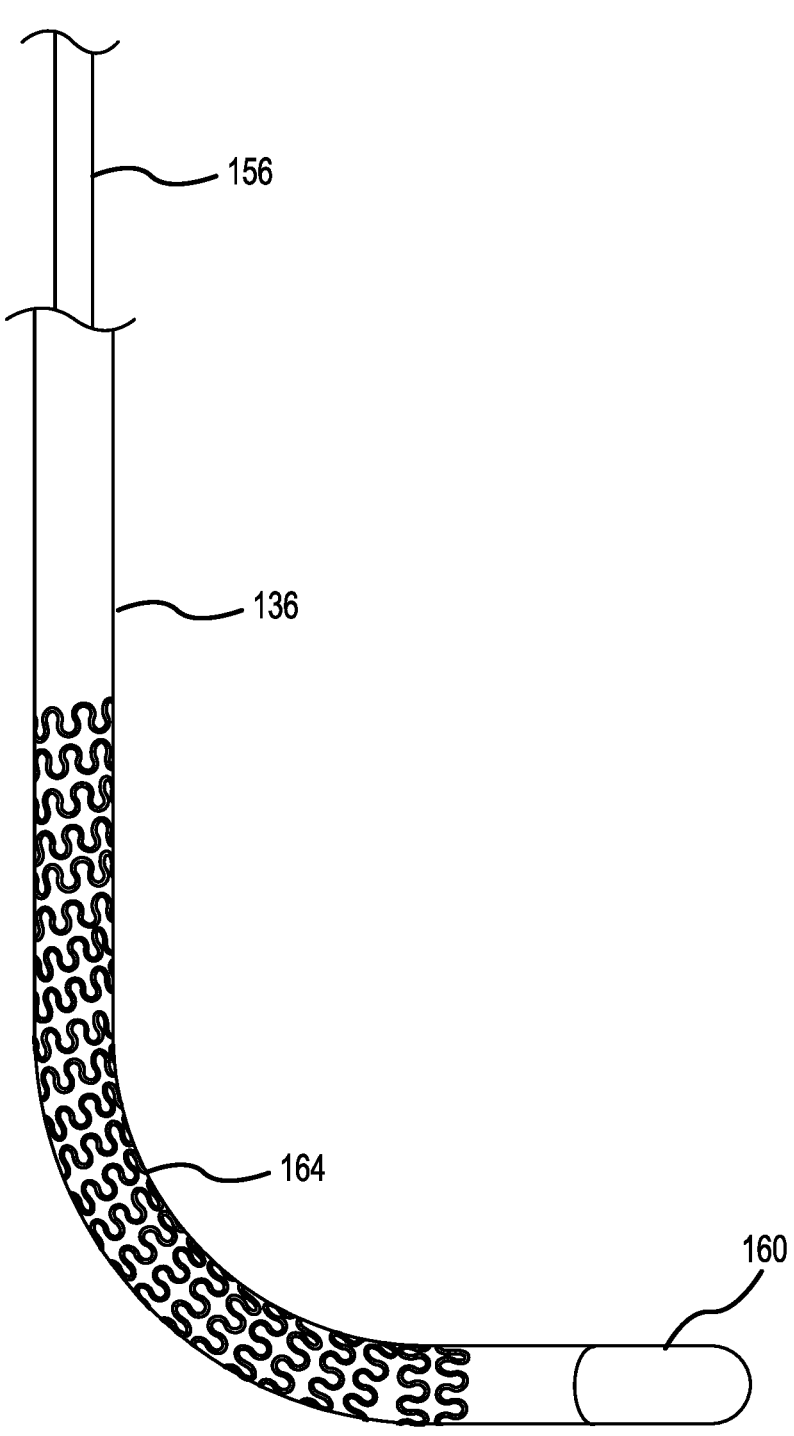
FIG. 1K is a side view of the J-shaped stylet inserted in the cylindrical electrode according to at least one embodiment of the present disclosure.

The first electrode 136 and/or the second electrode 140 may be or comprise hollow cylindrical tubing (e.g., stainless steel tubing, spring steel tubing, tubing comprising other metal alloys, etc.), and may extend from the proximal end 104 of the surgical tool 102 (e.g., from within the clamshell 112) toward the distal end 108 of the surgical tool 102. In other words, the first electrode 136 and/or the second electrode 140 may be or comprise conductive tubes that extend from the proximal end 104 of the surgical tool 102 toward the distal end of the distal end 108. The hollow space in the conductive tubing may allow other components to be stored in or pass through an interior of the conductive tubing of the first electrode 136 and/or the second electrode 140, which may better facilitate use of the surgical tool 102. In some embodiments, the first electrode 136 and/or the second electrode 140 may have small enough radii such that both the first electrode 136 and the second electrode 140 can fit through the interior radius of the cannula tube 124 when the surgical tool 102 is inserted into the surgical site. In some embodiments, the first electrode 136 and/or the second electrode 140 may be segmented. In other words, the first electrode 136 and/or the second electrode 140 may contain one or more helical cuts running along a portion or the entirety of a length thereof. Alternatively, the first electrode 136 and/or the second electrode 140 may be or comprise one or more braided segments. The braided segments may comprise braided wires or other polymers capable of conducting RF current. As shown in FIG. 1E, the second electrode 140 may have a helical cut running along a length thereof, while the first electrode 136 may contain segmented cuts along the surface thereof. The segmenting and/or braiding of the first electrode 136 and/or the second electrode 140 may permit the first electrode 136 and/or the second electrode 140 to be bent, deflected, or twisted when inserted into the target surgical site. For instance, as shown in FIG. 1K, braided segments 164 may allow the surgical tip 160 to bend relative to a straight portion of the first electrode 136. The flexibility of the first electrode 136 and/or the second electrode 140 may better enable the surgical tool 102 to be inserted through the cannula tube 124 and into the target surgical site.

A surgical tip 160 may be attached to a distal end of the first electrode 136. The surgical tip 160 may comprise a conductive material (e.g., one or more metal alloys, Nitinol, spring steel, stainless steel, etc.), such that the surgical tip 160 acts as an extension of the first electrode 136 when RF current flows through the first electrode 136. In other words, the surgical tip 160 may assist or facilitate the passage of RF current into the anatomical tissue at the surgical site by, for example, increasing the amount of surface area through which the RF current can flow. In such embodiments, the surgical tip 160 may be the only portion of the surgical tool 102 that contacts and/or conducts RF current into the anatomical tissue. Stated differently, the first electrode 136 may be completely insulated by the first layer of insulation 144 as depicted in FIG. 1E, while the surgical tip 160 is not surrounded by the first layer of insulation 144, functions as an electrode, and is able to pass the RF current into the anatomical tissue.

The first layer of insulation 144 may be or comprise insulative material (e.g., plastic, PVC, Teflon, rubber, Polyethylene terephthalate (PET) heat shrinkable material, Polyether Ether Ketone (PEEK) heat shrinkable material, polyimide, combinations thereof, etc.) capable of preventing RF current from passing from the first electrode 136 to other components within the surgical tool 102. Similarly, the protective barrier 148 may be or comprise insulative material, such as PET heat shrinkable material, that protects the second electrode 140 (e.g., prevents patient tissue or other patient anatomy from contacting the second electrode 140). In some embodiments, the protective barrier 148 may comprise heat shrinkable material and may be shrunk into the surface of the second electrode 140 before the surgical tool 102 is inserted into the cannula assembly 106.

In some embodiments, the components of the surgical tool 102 that enable ablation may be concentrically aligned and layered. For example, a metal core 152 may be the innermost component in the surgical tool 102 and may be circumferentially surrounded by the other ablation components. For example, the first electrode 136 may be the next layer of the surgical tool 102 that surrounds the metal core 152 (e.g., the metal core 152 is positioned within an inner radius of the first electrode 136). The first electrode 136 may have the first layer of insulation 144 wrapped therearound, the first layer of insulation 144 insulating the first electrode 136 from other components of the surgical tool 102. The next layer may include the second electrode 140 disposed around the first layer of insulation 144. In other words, the first electrode 136 and the first layer of insulation 144 may be disposed within the interior of the second electrode 140, with the first layer of insulation 144 electrically separating the first electrode 136 from the second electrode 140. The second electrode 140 may include the protective barrier 148 disposed therearound (e.g., the protective barrier 148 may be heat shrunk onto the outer surface of the second electrode 140). The length of each of the component extending toward the distal end 108 of the surgical tool 102 may be different for each component as to enable ablation. For instance, as illustrated in FIG. 1E, the surgical tip 160 may be the most distal point of the surgical tool 102, followed by the first electrode 136 and the first layer of insulation 144 therearound. The second electrode 140 may not extend as far toward the distal end of the surgical tool 102 as the first electrode 136, the first layer of insulation 144, and/or the surgical tip 160. The shortness of the second electrode 140 relative to the first electrode 136 may allow the surgical tip 160 (which may be an extension of the first electrode 136) to contact a first portion of the anatomical tissue to be ablated and allow the second electrode 140 to contact a different second portion of the anatomical tissue to be ablated, allowing the RF current to flow through the anatomical tissue. In some embodiments, the protective barrier 148 may only wrap around a portion of the second electrode 140, such that a portion of the second electrode 140 is exposed to the anatomical tissue when the surgical tool 102 is inserted into the surgical site to ablate the anatomical tissue, with the remaining portion of the second electrode 140 remaining shielded from the surgical environment by the protective barrier 148.

The pull handle 116 of the surgical tool 102 may be connected to the metal core 152. The metal core 152 may be or comprise Nitinol and may assist with providing structure to the surgical tool 102. In some embodiments, the metal core 152 may be disposed within the interior of the surgical tool 102 (e.g., within an interior radius of the first electrode 136 when the first electrode 136 is a hollow tube), and may configured to be extracted from the interior of the surgical tool 102. The metal core 152 may be attached to a J-shaped stylet 156. The J-shaped stylet 156 may be or comprise Nitinol or other material, and may be flexible or bendable. In some embodiments, the J-shaped stylet 156 may extend through a hole of the distal tip, as illustrated in FIGS. 1H and 1K. In such embodiments, the J-shaped stylet 156 may be fixed within the interior of the surgical tool 102 (e.g., the J-shaped stylet 156 is not removable) and may be used to guide the surgical tool 102 through the cannula tube 124 toward the target surgical site.

In some embodiments, both the metal core 152 and the J-shaped stylet 156 may be configured to be removed from the surgical tool 102 after the surgical tool 102 has been inserted into the cannula tube 124 and before performing an ablation of anatomical tissue. For example, the surgical tool 102 (along with the metal core 152 and the J-shaped stylet 156 disposed therein) may be inserted through the cannula handle 120 and the cannula tube 124 and into the target surgical site (e.g., the BVN of a vertebra). While inserting the surgical tool 102 into the target surgical site, the metal core 152 and the J-shaped stylet 156 may provide structure to the surgical tool 102, making it easier for the surgeon to insert the surgical tool 102. Once the surgical tool 102 reaches the target surgical site (e.g., the electrodes of the surgical tool 102 are positioned such that the anatomical tissue can be ablated), the metal core 152 and the J-shaped stylet 156 may be extracted from the surgical tool 102. For instance, a surgeon may pull on the pull handle 116 in a proximal direction (e.g., a direction away from the target surgical site), such that the metal core 152 and the J-shaped stylet 156 are extracted from or slide out of the interior of the surgical tool 102 (e.g., from within an interior of the first electrode 136 when the first electrode 136 is a hollow tube). In some embodiments, the metal core 152 and the J-shaped stylet 156 may be sufficiently thin and/or narrow such that the metal core 152 and the J-shaped stylet 156 can be extracted from the surgical tool 102 without contacting, damaging, or otherwise interfering with the other components of the surgical tool 102 (e.g., the first electrode 136, the thermocouple 132, etc.). The removal of the metal core 152 and the J-shaped stylet 156 may reduce the thermal mass of the surgical tool 102, such that the first electrode 136 and the second electrode 140 can be heated to a desired temperature faster and the time needed to complete the ablation may be reduced.

In some embodiments, the metal core 152 and/or the J-shaped stylet 156 may alternatively be configured to not be removed from the interior of the surgical tool 102, and rather may be designed to remain within the surgical tool 102. In such embodiments, the metal core 152 and the J-shaped stylet 156 may be connected to a fluid reservoir system (not shown) that may be used to cool the surgical tool 102. For instance, the metal core 152 and the J-shaped stylet 156 may be hollow to permit a coolant (e.g., water, sterilized water, saline, etc.) to flow through the metal core 152 and/or the J-shaped stylet 156. In some embodiments, the coolant may draw heat from the metal core 152 and, by extension, the first electrode 136. The extraction of heat by the coolant may reduce the probability of charring of the anatomical tissue being ablated. The coolant may then be extracted from the surgical tool 102 in the space between the interior of the first electrode 136 and the exterior of the metal core 152. In such embodiments, the first electrode 136 may be fluid tight, such that the coolant does not escape from the interior of the first electrode 136 and spill into the surgical site. The coolant may be flowed into and out of the surgical tool 102 through one or more tubes (not shown) connected to a fluid reservoir. The fluid reservoir may contain separate reservoirs for fresh coolant to be pumped into the surgical tool 102 and for the spent coolant existing the surgical tool 102. The fluid reservoir may utilize one or more pumps connected to the reservoirs to pump the coolant through the surgical tool 102.

Turning to FIGS. 2A-2J, illustrative aspects of a surgical assembly 200 are depicted in accordance with at least one embodiment of the present disclosure. The surgical assembly 200 may include a surgical tool 202 and a cannula assembly 206. Notwithstanding the foregoing, the surgical assembly 200 may include additional or alternatively components.

The surgical tool 202 may span from a proximal end 204 to a distal end 208 connected by an elongated sheath 205. The elongated sheath 205 may be a hollow, cylindrical tubing that provides structural support to the surgical tool 202. The surgical tool 202 may contain components that enable bipolar electrosurgery. For instance, the surgical tool 202 may include a first electrode 236 and a second electrode 240 connected to an RF current generator or other power source such that the electrodes can be used to ablate anatomical tissue. The surgical tool 202 may include a cable 228 that carries wiring 230 from the RF current generator to the first electrode 236 and the second electrode 240. In some embodiments, the first electrode 236 may be similar to or the same as the first electrode 136, and the second electrode 240 may be similar to or the same as the second electrode 140. In some embodiments, both the first electrode 236 and the second electrode 240 may be cylindrical tubes that are layered concentrically but extend different distances toward the distal end 208 of the surgical tool 202. For example, the first electrode 236 may be disposed within the inner diameter of the second electrode 240 and may extend further toward the distal end 208 (e.g., the first electrode 236 is longer than the second electrode 240), such that both the first electrode 236 and the second electrode 240 are exposed to the anatomical tissue to be ablated. The first electrode 236 may be surrounded by a first layer of insulation 244 that may be similar to or the same as the first layer of insulation 144. The first layer of insulation 244 may electrically isolate the first electrode 236 from the other components of the surgical tool 202. In other words, the first layer of insulation 244 may enable the RF current to pass from the first electrode 236 into the anatomical tissue by preventing the RF current from passing into the second electrode 240 without first passing through the anatomical tissue. The second electrode 240 may also include a protective barrier 248 disposed there-around. The second electrode 240 may be similar to or the same as the protective barrier 148.

The distal end 208 may include a ceramic tip 260. The ceramic tip 260 may be disposed on the distal end of the first electrode 236 and may facilitate the entry of the surgical tool 202 into the target surgical site. The ceramic tip 260 may be a thermally and/or electrically insulative component. Stated differently, the ceramic tip 260 may not conduct heat and/or electric current. In other embodiments, the ceramic tip 260 may comprise conductive material (e.g., metal alloys, Nitinol, etc.), such that the ceramic tip 260 can operate as an extension of the first electrode 236. In some embodiments, the ceramic tip 260 may comprise a trocar or other tip that can be used to cut or burrow into anatomical tissue (e.g., bone).

Figure 2A:
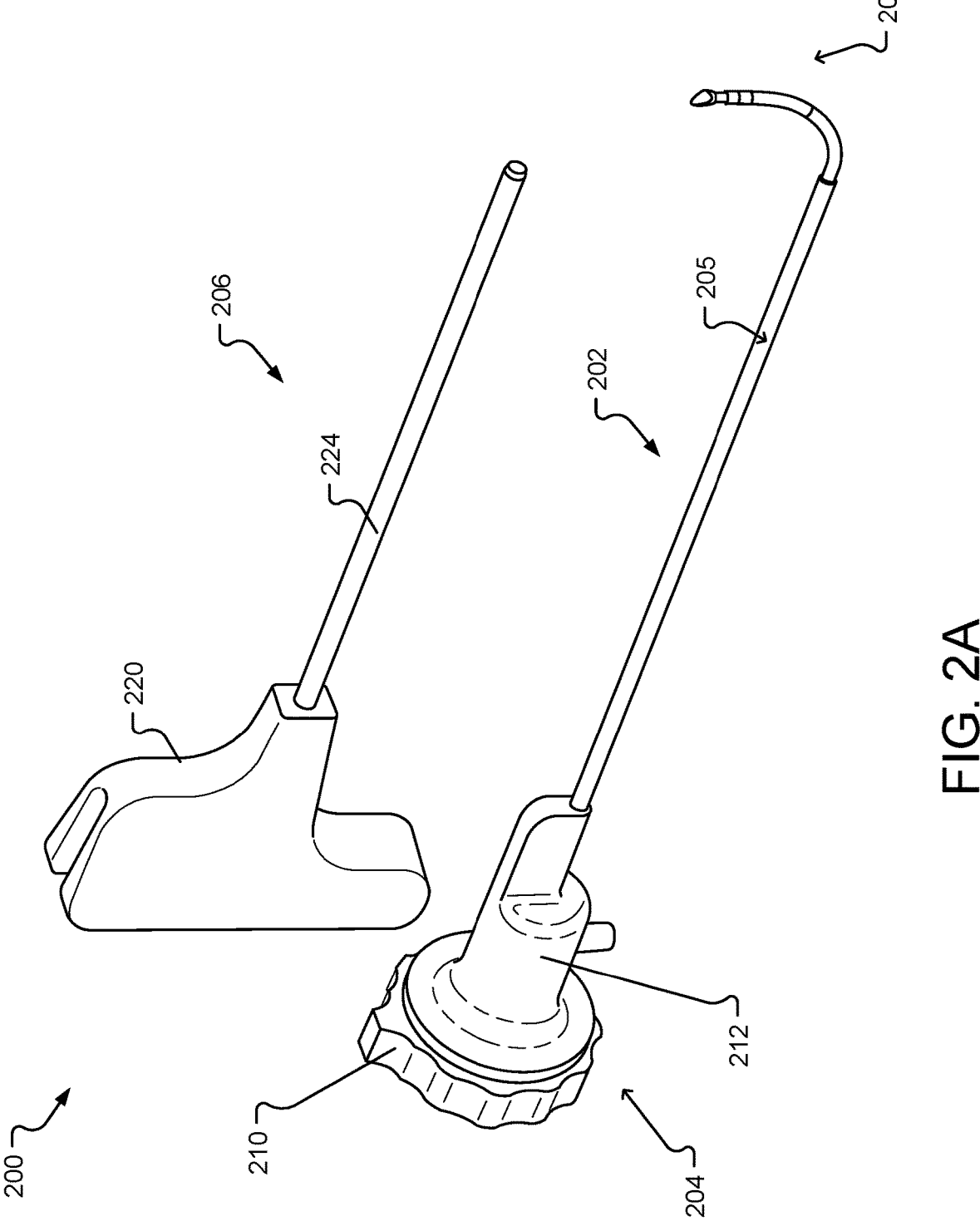
FIG. 2A is an isometric view of components of a second surgical assembly according to at least one embodiment of the present disclosure.
Figure 2B:
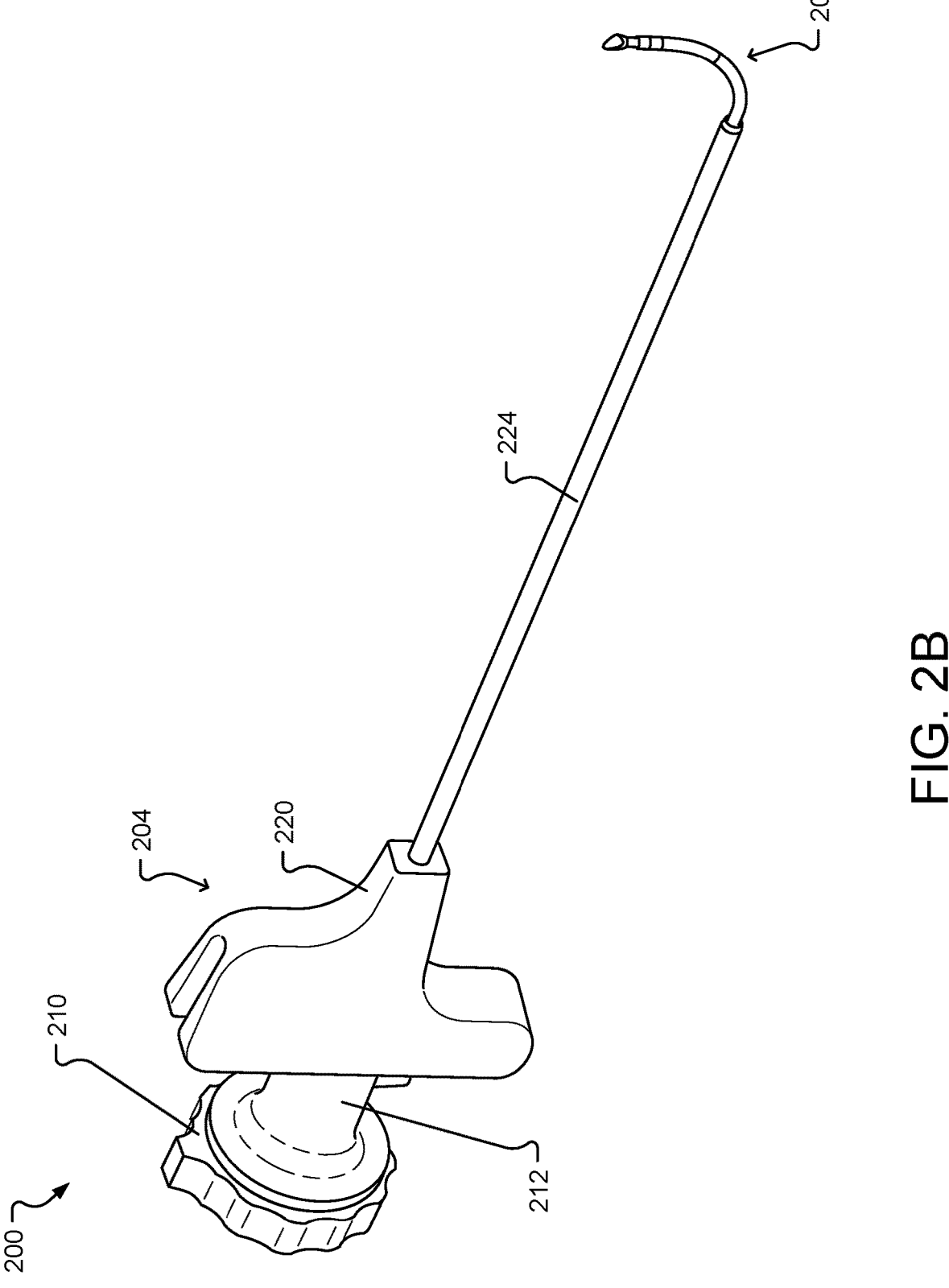
FIG. 2B is an isometric view of the second surgical assembly according to at least one embodiment of the present disclosure.
Figure 2C:
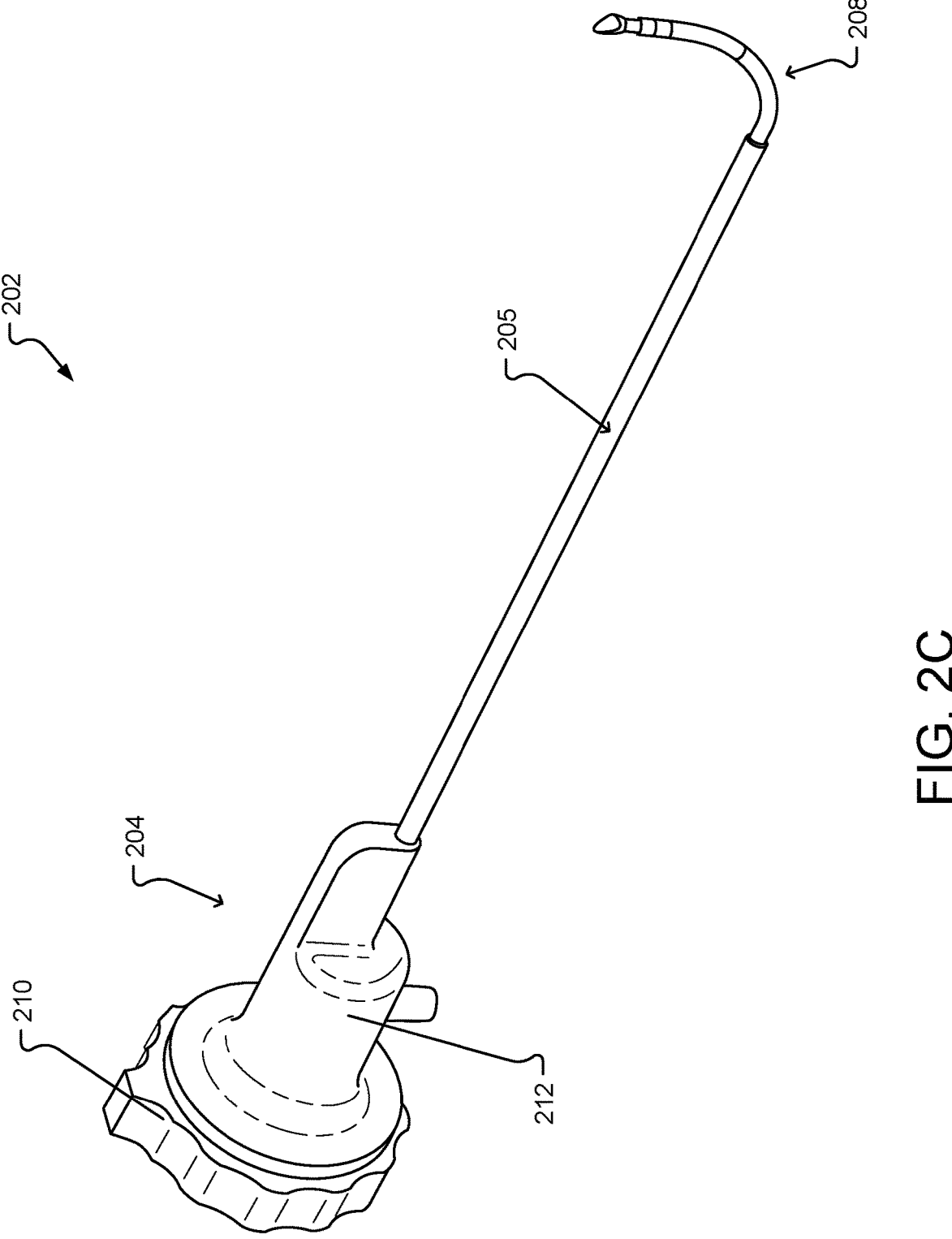
FIG. 2C is an isometric view of a second surgical tool of the second surgical assembly according to at least one embodiment of the present disclosure.
Figure 2D:
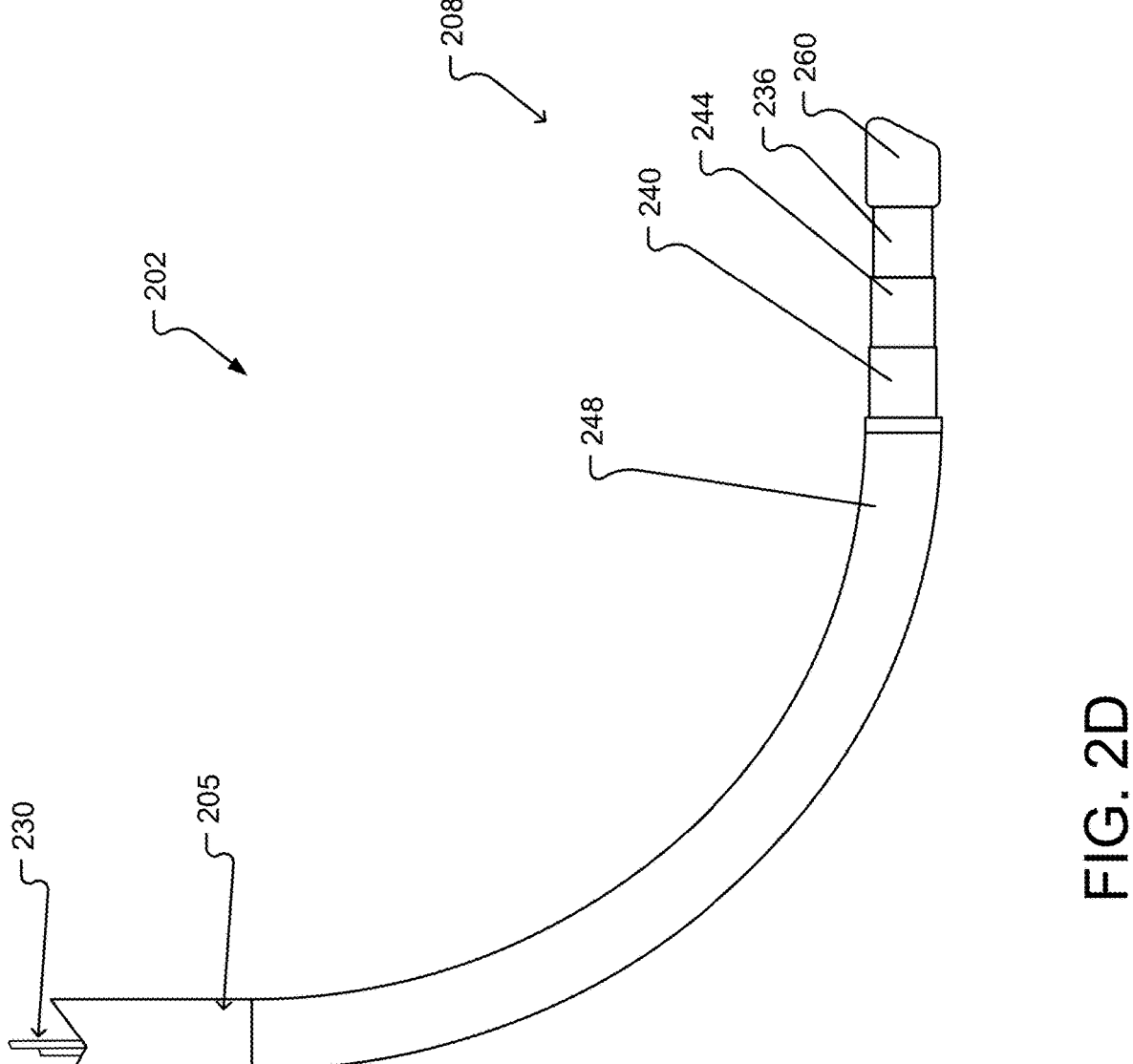
FIG. 2D is a side view of a distal end of the second surgical assembly according to at least one embodiment of the present disclosure.
Figure 2E:
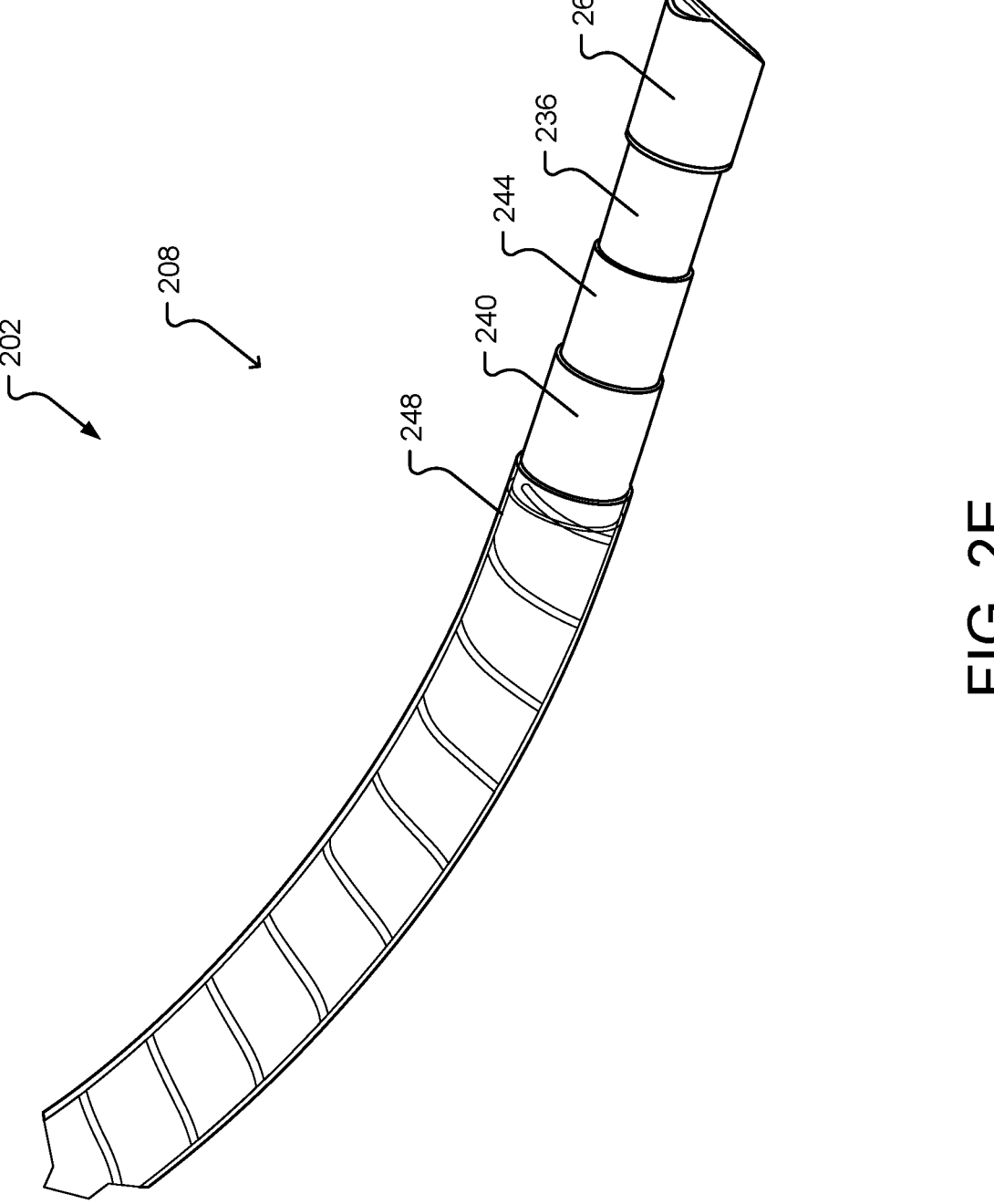
FIG. 2E is a detailed isometric view of the distal end of the second surgical assembly according to at least one embodiment of the present disclosure.
Figure 2F:
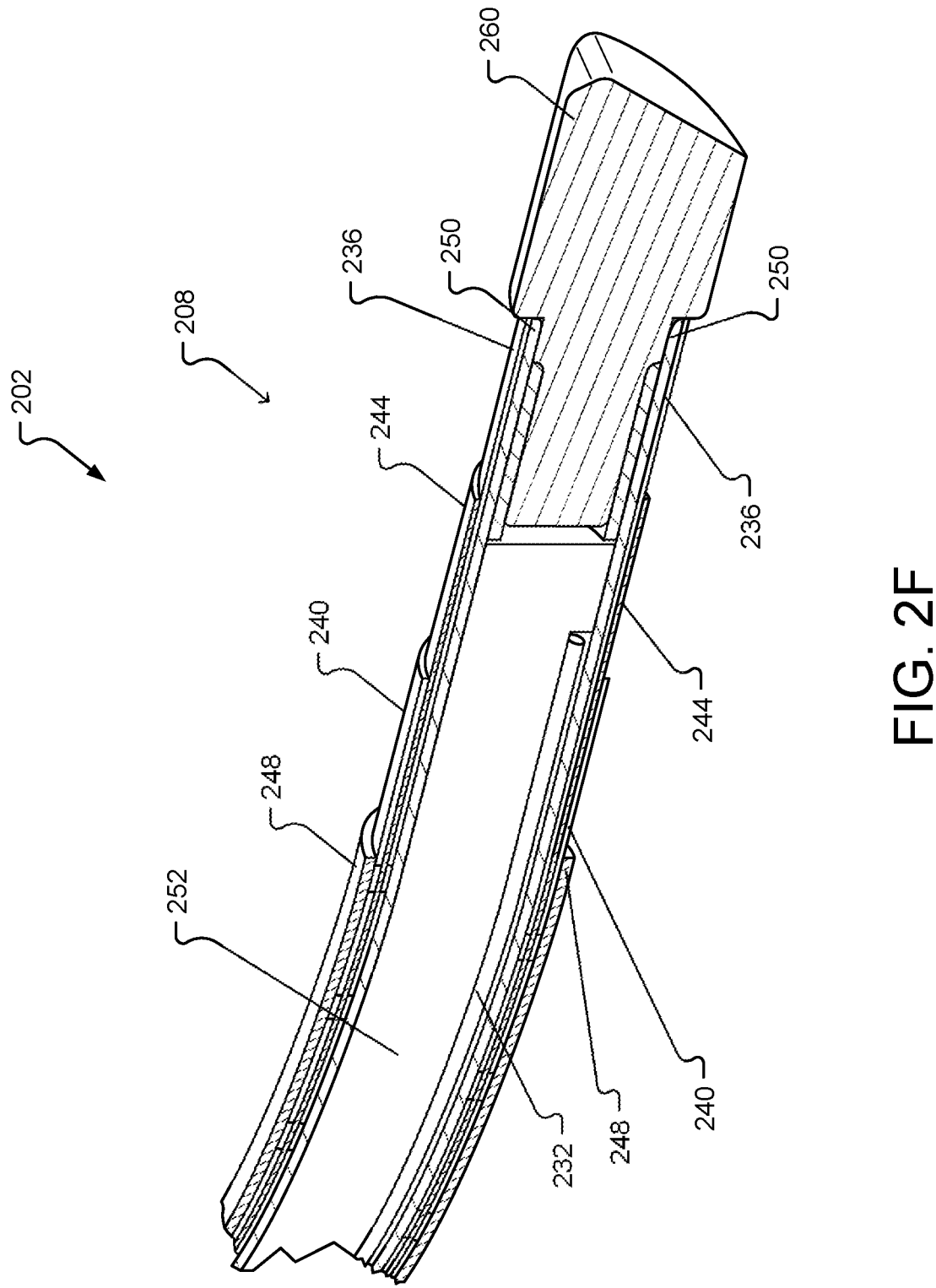
FIG. 2F is a cross section view of the distal end of the second surgical assembly according to at least one embodiment of the present disclosure.
Figure 2G:
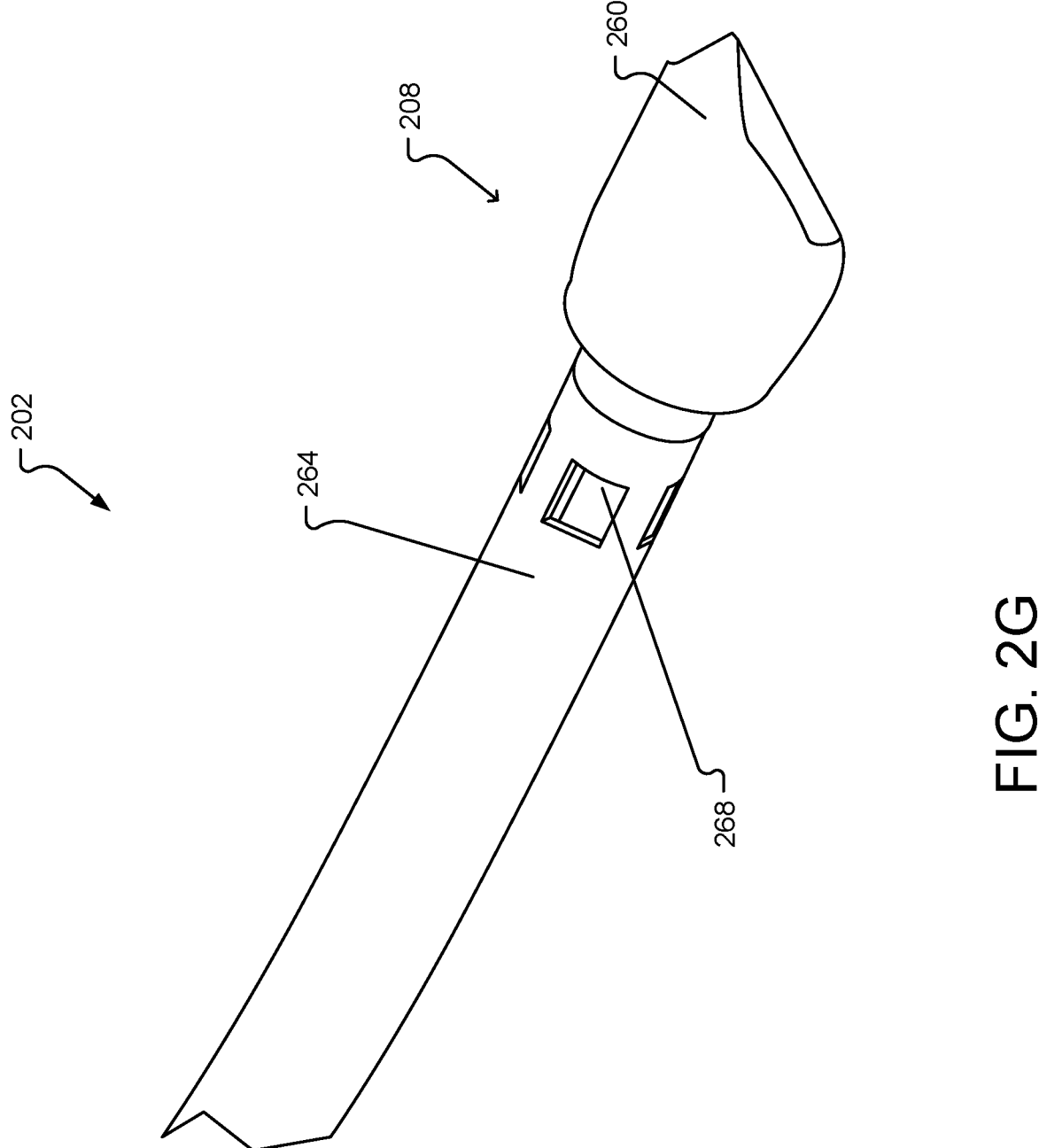
FIG. 2G is an isometric view of components of the second surgical assembly according to at least one embodiment of the present disclosure.
Figure 2H:
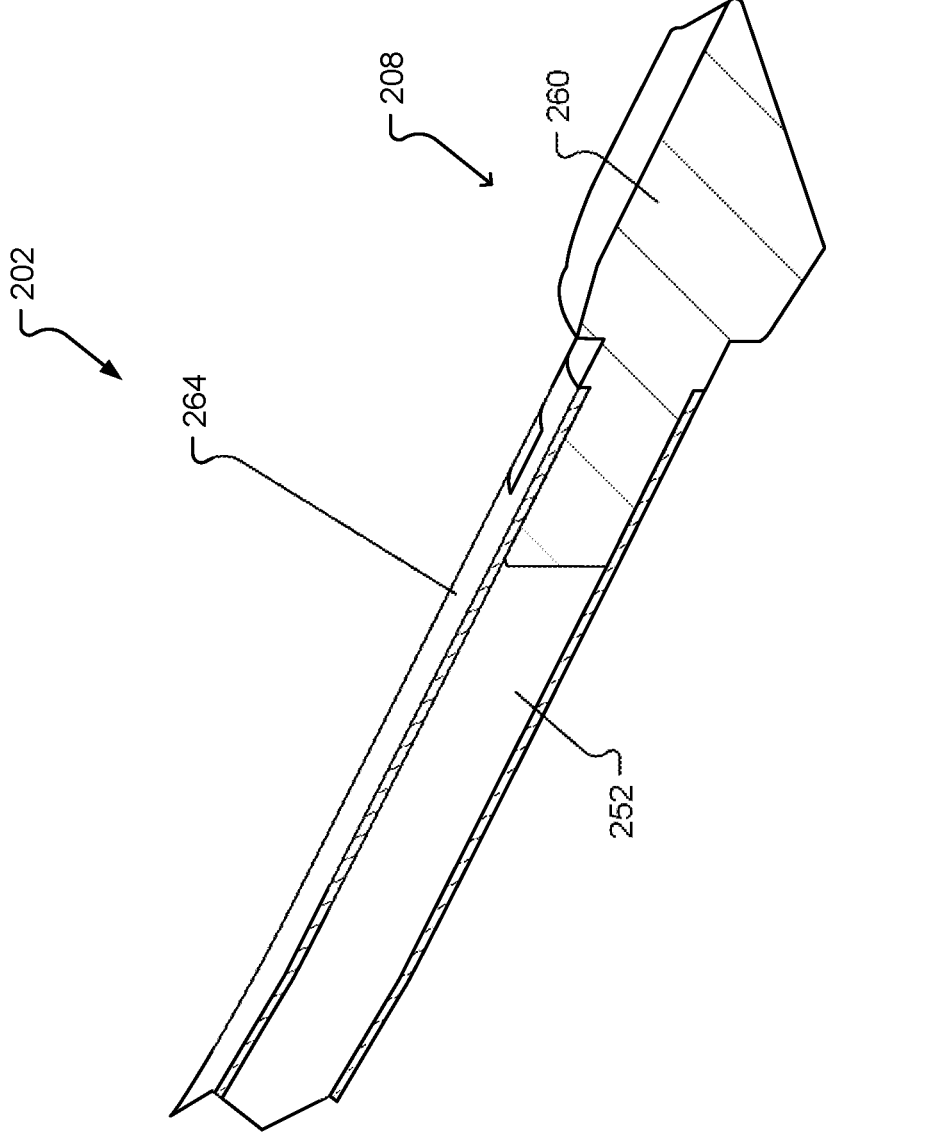
FIG. 2H is a cross section view of the components of the second surgical assembly according to at least one embodiment of the present disclosure.
Figure 2I:
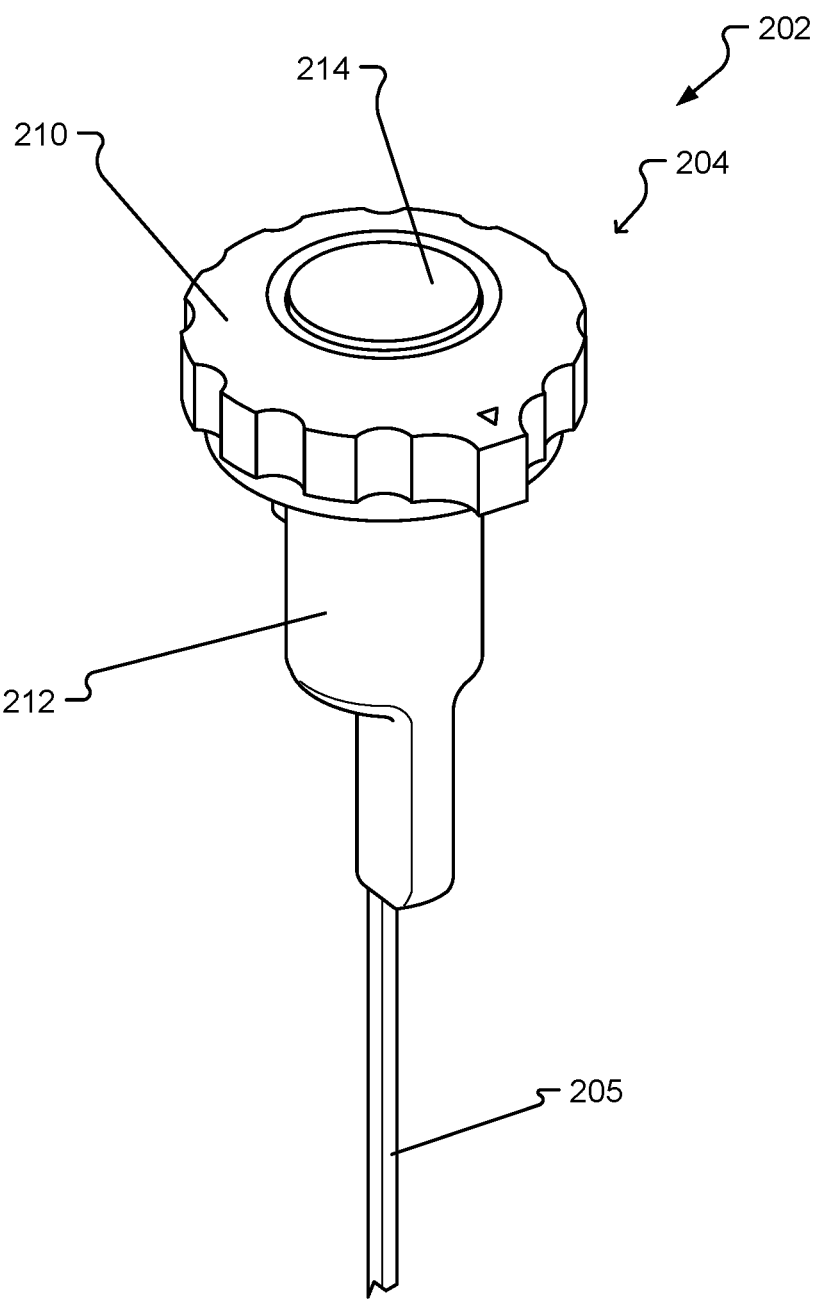
FIG. 2I is an isometric view of a proximal end of the second surgical assembly according to at least one embodiment of the present disclosure.
Figure 2J:
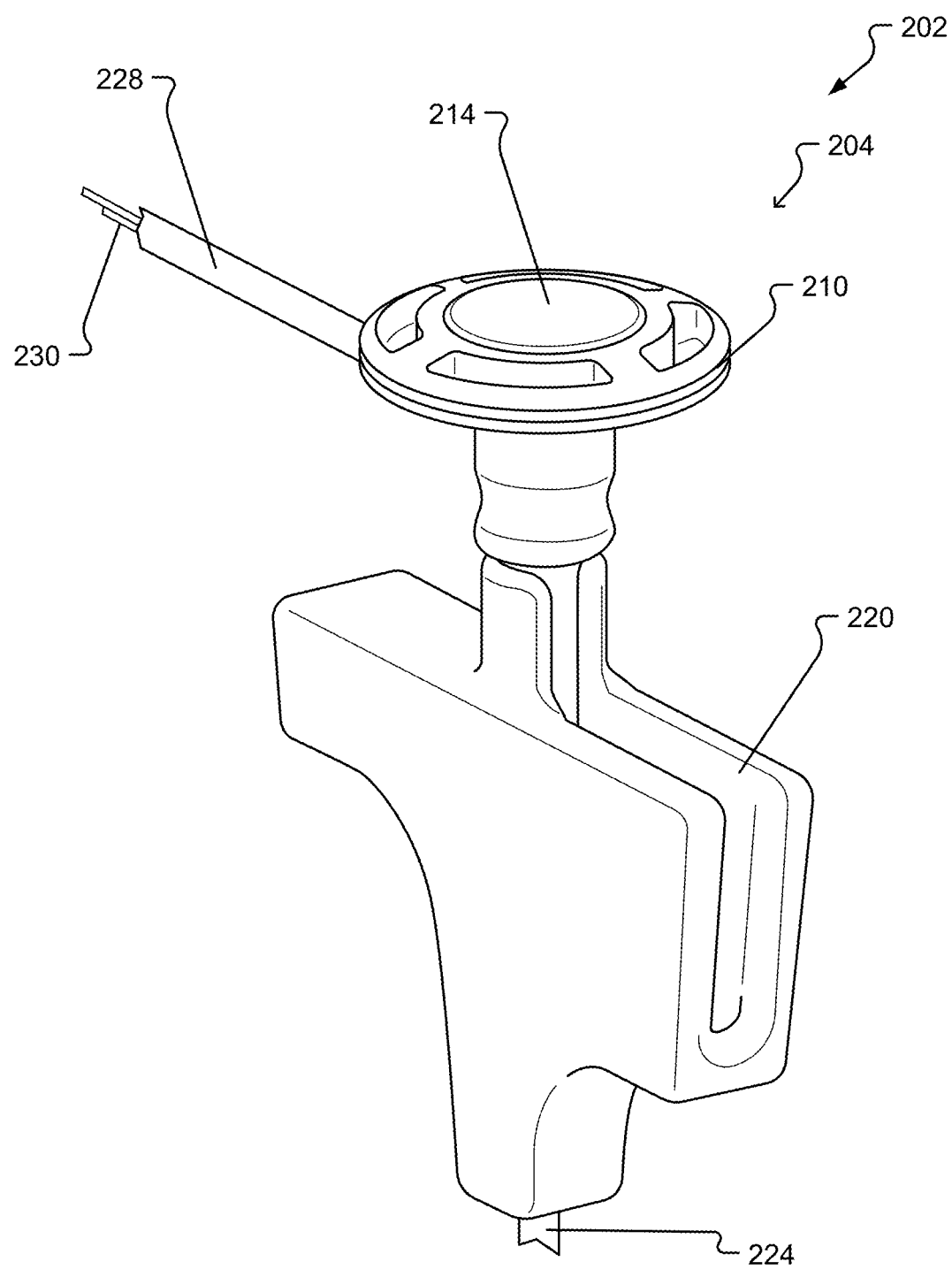
FIG. 2J is an isometric view of an alternative proximal end of the second surgical assembly according to at least one embodiment of the present disclosure.

In some embodiments, the ablation components of the surgical tool 202 may be layered on top of one another and may extend different distances relative to one another, as depicted in FIGS. 2D-2F. The protective barrier 248 may form the outermost layer (e.g., a layer with the largest radius) and may wrap around the elongated sheath 205 and/or the second electrode 240, which may be a hollow, metal, cylindrically shaped tube. The protective barrier 248 may form an electrically insulative layer to protect the elongated sheath 205 and/or the second electrode 240 from contacting the surgical environment, and may also provide a barrier to prevent anatomical tissue or debris (e.g., blood or other bodily fluids) from contacting the second electrode 240 when the surgical tool 202 is inserted into the patient. The second electrode 240 may extend further than the protective barrier 248, however, such that a portion of the second electrode 240 can contact the surrounding anatomical tissue. The second electrode 240 may contain within its inner radius a first layer of insulation 244. The first layer of insulation 244 may electrically isolate the second electrode 240 from the first electrode 236, and may extend further toward the distal end 208 of the surgical tool 202 than the second electrode 240. The first layer of insulation 244 may be wrapped around the first electrode 236, which may be a hollow, metal, cylindrically shaped tube, such that both the first electrode 236 and the first layer of insulation 244 are contained within the interior portion of the second electrode 240. The first electrode 236 may extend further than the first layer of insulation 244 in the distal end 208 of the surgical tool 202 and may contain a metal core 252 therein (e.g., within the inner radius of the first electrode 236). The metal core 252 may be a solid metallic material (e.g., Nitinol) that provides structural support to the first electrode 236. In some embodiments, the metal core 252 may be segmented, or may otherwise be flexible or J-shaped such that the distal end 208 is flexible relative to the elongated sheath 205. In one embodiment, the metal core 252 may be similar to or the same as the metal core 152 and/or the J-shaped stylet 156. The first electrode 236 and/or the metal core 252 may be connected to the ceramic tip 260. In some embodiments, a second layer of insulation 250 may be disposed between and electrically isolate the first electrode 236 and the metal core 252, as shown in the cross section view of FIG. 2F.

In some embodiments, the metal core 252 may include a casing 264. The casing 264 may be or comprise the same material as the metal core 252 (e.g., Nitinol) and may be coupled with the ceramic tip 260 with one or more interlocking keys 268. Nitinol is an example of a shape-memory alloy that retains shape after being stressed, such as when receiving a heat treatment. In other words, Nitinol may undergo a stress-induced transformation (e.g., via heating of the material), such that the metal core 252 can be thermally formed into a J-shape (or any other shape). In some embodiments, the metal core 252 may be or comprise other shape-memory alloys (e.g., copper-aluminium-nickel alloys, iron-manganese-silicon alloys, etc.). Additionally or alternatively, the casing 264 may include one or more seams that are welded shut once the casing 264 is coupled with the ceramic tip 260 to help prevent the two from decoupling. The interlocking keys 268 may be disposed on the outer surface of the ceramic tip 260, and may slot into one or more slots provided by the casing 264. In one embodiment, the interlocking keys 268 and the ceramic tip 260 may be formed as a single component capable of being attached and detached from the casing 264. In other embodiments, the ceramic tip 260 and the interlocking keys 268 may be connected to one another with threads (e.g., the ceramic tip 260 is threaded and screws into the interlocking keys 268), with a cure bond, and/or with a thermal bond (e.g., the ceramic tip 260 and the interlocking keys 268 are partially or wholly fused together by applying heat). The metal core 252 and/or the casing 264 may run from the ceramic tip 260 back to the proximal end 204, with the metal core 252 configured to be removed from the surgical tool 202 before beginning ablation of the anatomical tissue. In some embodiments, the ceramic tip 260 may be radiopaque or otherwise comprise radiopaque material such that the ceramic tip 260 appears opaque on surgical images (e.g., opaque on 2D and/or 3D CT scans, opaque on fluoroscopic images or other X-ray images, etc.).

The surgical assembly 200 may also include a thermocouple 232 that runs from the proximal end 204 of the surgical tool 202 into the distal end 208. In some embodiments, the thermocouple 232 may be similar to or the same as the thermocouple 132. The thermocouple 232 may generate a measurement or reading that indicates a temperature of the component the thermocouple 232 contacts. For instance, the thermocouple 232 may contact the first electrode 236 and generate a temperature reading during ablation of anatomical tissue. The reading generated by the thermocouple 232 may be used (e.g., by a system 300 and/or a surgeon) to adjust the power generated by the RF current source (e.g., a generator) to increase or decrease the amount of RF current (and by consequence the temperature) of the first electrode 236. Additionally or alternatively, the thermocouple 232 may also generate readings associated with other ablation components. For example, multiple thermocouples may each be disposed on or proximate the second electrode 240, the metal core 252, the ceramic tip 260 in cases where the ceramic tip 260 is electrically and/or thermally conductive, and/or the casing 264 to generate temperature measurements thereof.

The cannula assembly 206 may include a cannula handle 220 and a cannula tube 224. In some embodiments, the cannula handle 220 may be similar to or the same as the cannula handle 120 and the cannula tube 224 may be similar to or the same as the cannula tube 124. In some embodiments, to access the target surgical site, the surgeon or physician may use both the surgical tool 202 and the cannula assembly 206 in conjunction with one another. Stated differently, unlike the surgical assembly 100 which may provide the cannula assembly 106 to access the surgical site and then insert the surgical tool 102 into the surgical site through the cannula assembly 106, the surgical assembly 200 may allow a physician to use of both the surgical tool 202 coupled with the cannula assembly 206 in accessing the surgical site. For example, to access the target surgical site (e.g., a vertebra), the surgeon may align the surgical assembly 200 relative to the target surgical site and strike a strike zone 214 disposed on the proximal end of the surgical tool 202. In such embodiments, the cannula assembly 206 may be aligned with the patient anatomy (e.g., a vertebra), such that by striking the cannula assembly 206, the ceramic tip 260 of the surgical tool 202 bores into the patient anatomy. The strike zone 214 may be mechanically coupled to the elongated sheath 205, the metal core 252, and/or the casing 264. When the surgeon strikes the strike zone 214 (e.g., with a hammer), the force applied by the hammer may be transferred through the elongated sheath 205, the metal core 252, and or the casing 264 and applied to the ceramic tip 260. The ceramic tip 260 may comprise a sharp edge (e.g., a trocar) such that the force causes the ceramic tip 260 to bore through anatomical tissues (e.g., bone, soft tissues, etc.). In some embodiments, one or more imaging devices may be used to determine the pose (e.g., position and/or orientation) of the ceramic tip 260 relative to the target surgical site. The surgeon may then adjust the surgical assembly 200 and/or components thereof and repeat the hammering until the ceramic tip 260 has reached the target surgical site.

In at least one embodiment, the ceramic tip 260 may be steerable. In such embodiments, the strike zone 214 may be at least partially disposed within a dial indicator 210. The dial indicator 210 may be a rotatable handle disposed on the proximal end 204 of the surgical tool 202 that is mechanically coupled with the strike zone 214, the elongated sheath 205, the metal core 252, and/or the casing 264. The dial indicator 210 may be twisted or rotated by the surgeon or physician to adjust the pose of the ceramic tip 260. For example, if the surgeon wishes to move the ceramic tip 260 in a first direction, the surgeon may twist the dial indicator 210 in a first direction (e.g., clockwise) and then strike the strike zone 214. The twist of the dial indicator 210 and subsequent application of force on the strike zone 214 may cause the components mechanically coupled to the dial indicator 210 (e.g., the elongated sheath 205, the metal core 252, and/or the casing 264) to move in the first direction which may in turn cause the ceramic tip 260 to move in the first direction. Larger turns of the dial indicator 210 in the first direction may increase the frictional force between the components connected to the dial indicator 210 and the surgical environment into which the surgical tool 202 is inserted, causing the ceramic tip 260 to turn further in the first direction when the strike zone 214 is struck. Similarly, if the surgeon were to turn the dial indicator 210 in a second direction (e.g., counterclockwise), the ceramic tip 260 may deflect in a second direction when the strike zone 214 is struck. Subsequent adjustments of the dial indicator 210 along with the curved shape of the distal end 208 may enable the surgeon to burrow through anatomical tissues to reach the target surgical site.

Figure 3:
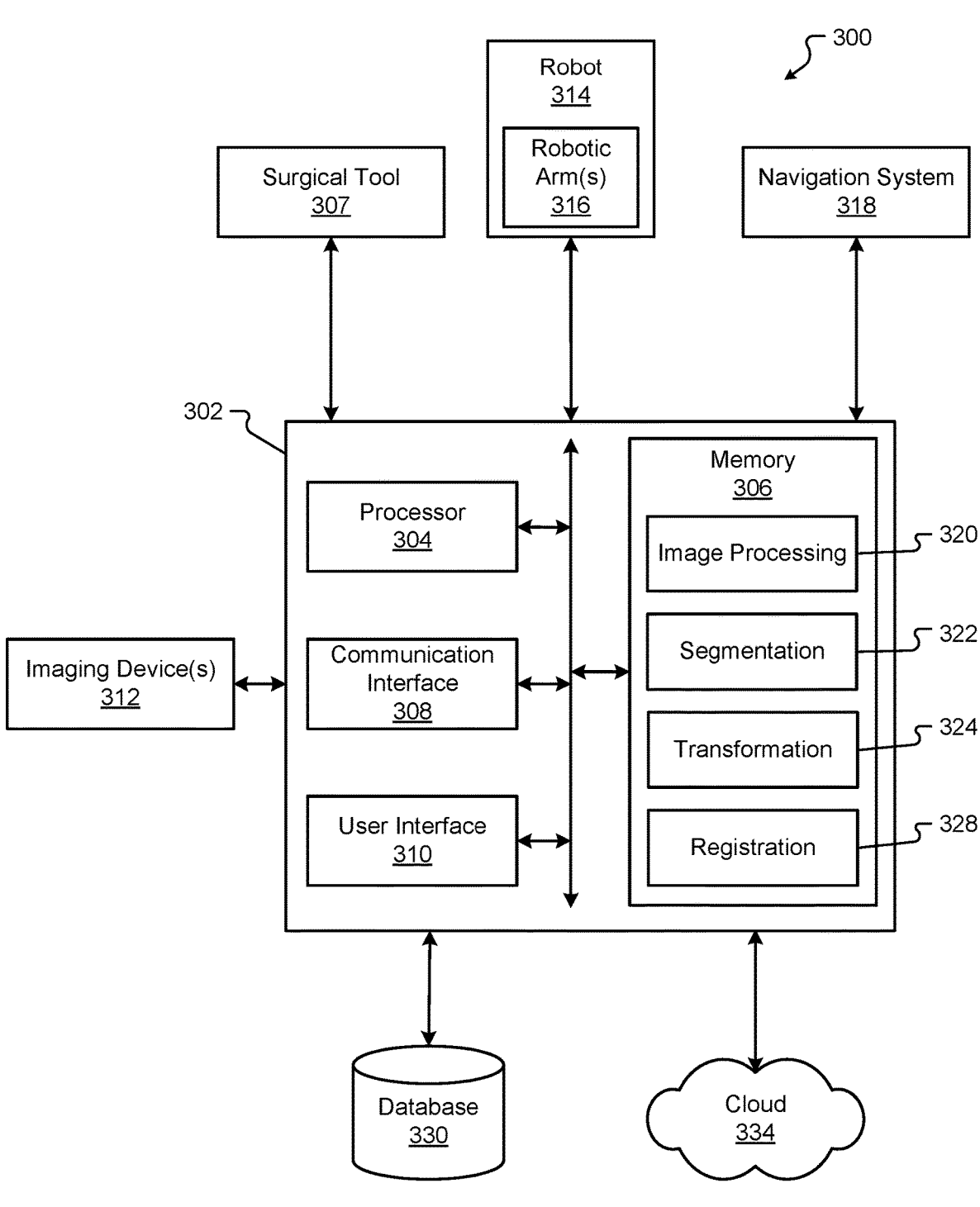
FIG. 3 is a block diagram of a system according to at least one embodiment of the present disclosure.

Turning now to FIG. 3, a block diagram of a system 300 according to at least one embodiment of the present disclosure is shown. The system 300 may be used to facilitate the surgical ablation of anatomical tissues, to assist a surgeon with navigation during the surgery or surgical procedure, and/or to carry out one or more other aspects of the one or more methods disclosed herein. The system 300 comprises a computing device 302, a surgical tool 307, one or more imaging devices 312, a robot 314, a navigation system 318, a database 330, and/or a cloud or other network 334. Systems according to other embodiments of the present disclosure may comprise more or fewer components than the system 300. For example, the system 300 may not include the imaging device 312, the robot 314, the navigation system 318, one or more components of the computing device 302, the database 330, and/or the cloud 334.

The computing device 302 comprises a processor 304, a memory 306, a communication interface 308, and a user interface 310. Computing devices according to other embodiments of the present disclosure may comprise more or fewer components than the computing device 302.

The processor 304 of the computing device 302 may be any processor described herein or any similar processor. The processor 304 may be configured to execute instructions stored in the memory 306, which instructions may cause the processor 304 to carry out one or more computing steps utilizing or based on data received from the imaging device 312, the robot 314, the navigation system 318, the database 330, and/or the cloud 334.

The memory 306 may be or comprise RAM, DRAM, SDRAM, other solid-state memory, any memory described herein, or any other tangible, non-transitory memory for storing computer-readable data and/or instructions. The memory 306 may store information or data useful for completing, for example, any step of the method 500 described herein, or of any other methods. The memory 306 may store, for example, instructions and/or machine learning models that support one or more functions of the robot 314. For instance, the memory 306 may store content (e.g., instructions and/or machine learning models) that, when executed by the processor 304, enable image processing 320, segmentation 322, transformation 324, and/or registration 328. Such content, if provided as in instruction, may, in some embodiments, be organized into one or more applications, modules, packages, layers, or engines. Alternatively or additionally, the memory 306 may store other types of content or data (e.g., machine learning models, artificial neural networks, deep neural networks, etc.) that can be processed by the processor 304 to carry out the various method and features described herein. Thus, although various contents of memory 306 may be described as instructions, it should be appreciated that functionality described herein can be achieved through use of instructions, algorithms, and/or machine learning models. The data, algorithms, and/or instructions may cause the processor 304 to manipulate data stored in the memory 306 and/or received from or via the imaging device 312, the robot 314, the database 330, and/or the cloud 334.

The surgical tool 307 may be any surgical tool discussed herein (e.g., a surgical tool 102, a surgical tool 202, etc.) that may be used by a surgeon during a surgery or surgical procedure. In some embodiments, the surgical tool 307 may be in communication with the computing device 302, the imaging devices 312, the navigation system 318, and/or any other component of the system 300. For example, the surgical tool 307 may include a thermocouple (e.g., a thermocouple 132, a thermocouple 232, etc.) that may communicate readings to the computing device 302. The computing device 302 may use the readings to generate one or more temperature measurements of the surgical tool 307 and provide those measurements to the surgeon (e.g., rendering the temperature measurements to a display).

The computing device 302 may also comprise a communication interface 308. The communication interface 308 may be used for receiving image data or other information from an external source (such as the imaging device 312, the robot 314, the navigation system 318, the database 330, the cloud 334, and/or any other system or component not part of the system 300), and/or for transmitting instructions, images, or other information to an external system or device (e.g., another computing device 302, the imaging device 312, the robot 314, the navigation system 318, the database 330, the cloud 334, and/or any other system or component not part of the system 300). The communication interface 308 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 308 may be useful for enabling the computing device 302 to communicate with one or more other processors 304 or computing devices 302, whether to reduce the time needed to accomplish a computing-intensive task or for any other reason.

The computing device 302 may also comprise one or more user interfaces 310. The user interface 310 may be or comprise a keyboard, mouse, trackball, monitor, television, screen, touchscreen, and/or any other device for receiving information from a user and/or for providing information to a user. The user interface 310 may be used, for example, to receive a user selection or other user input regarding any step of any method described herein. Notwithstanding the foregoing, any required input for any step of any method described herein may be generated automatically by the system 300 (e.g., by the processor 304 or another component of the system 300) or received by the system 300 from a source external to the system 300. In some embodiments, the user interface 310 may be useful to allow a surgeon or other user to modify instructions to be executed by the processor 304 according to one or more embodiments of the present disclosure, and/or to modify or adjust a setting of other information displayed on the user interface 310 or corresponding thereto.

Although the user interface 310 is shown as part of the computing device 302, in some embodiments, the computing device 302 may utilize a user interface 310 that is housed separately from one or more remaining components of the computing device 302. In some embodiments, the user interface 310 may be located proximate one or more other components of the computing device 302, while in other embodiments, the user interface 310 may be located remotely from one or more other components of the computing device 302.

The imaging device 312 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 312, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 312 may be used to obtain first image data (e.g., a first image) at a first time, and a second imaging device 312 may be used to obtain second image data (e.g., a second image) at a second time after the first time. The imaging device 312 may be capable of taking a 2D image or a 3D image to yield the image data. The imaging device 312 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 312 suitable for obtaining images of an anatomical feature of a patient. The imaging device 312 may be contained entirely within a single housing, or may comprise a transmitter/emitter and a receiver/detector that are in separate housings or are otherwise physically separated.

In some embodiments, the imaging device 312 may comprise more than one imaging device 312. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 312 may be operable to generate a stream of image data. For example, the imaging device 312 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

In some embodiments, the imaging device 312 may provide real-time feeds (e.g., live video feeds) to the surgeon or other users (e.g., members of a surgical staff) during a surgery or surgical procedure. For example, the surgical tool 307 may be used to enter an anatomical element (e.g., a vertebra) and the imaging device 312 may provide footage of such an entry. The surgeon or other users may be able to view the footage and determine whether the surgical tool 307 is being correctly inserted into the anatomical element. Additionally or alternatively, when the physician is steering the surgical tool 307 (e.g., using a hammer to strike a strike zone 214 to steer a ceramic tip 260), the physician may be able to view the data produced by the imaging device 312 real-time to determine whether the ceramic tip 260 is being directed correctly to reach the target surgical site.

The robot 314 may be any surgical robot or surgical robotic system. The robot 314 may be or comprise, for example, the Mazor X™ Stealth Edition robotic guidance system. The robot 314 may be configured to position the imaging device 312 at one or more precise position(s) and orientation(s), and/or to return the imaging device 312 to the same position(s) and orientation(s) at a later point in time. The robot 314 may additionally or alternatively be configured to manipulate a surgical tool (whether based on guidance from the navigation system 318 or not) to accomplish or to assist with a surgical task. In some embodiments, the robot 314 may be configured to hold and/or manipulate an anatomical element during or in connection with a surgical procedure. The robot 314 may comprise one or more robotic arms 316. In some embodiments, the robotic arm 316 may comprise a first robotic arm and a second robotic arm, though the robot 314 may comprise more than two robotic arms. In some embodiments, one or more of the robotic arms 316 may be used to hold and/or maneuver the imaging device 312. In embodiments where the imaging device 312 comprises two or more physically separate components (e.g., a transmitter and receiver), one robotic arm 316 may hold one such component, and another robotic arm 316 may hold another such component. Each robotic arm 316 may be positionable independently of the other robotic arm. The robotic arms 316 may be controlled in a single, shared coordinate space, or in separate coordinate spaces.

The robot 314, together with the robotic arm 316, may have, for example, one, two, three, four, five, six, seven, or more degrees of freedom. Further, the robotic arm 316 may be positioned or positionable in any pose, plane, and/or focal point. The pose includes a position and an orientation. As a result, an imaging device 312, surgical tool, or other object held by the robot 314 (or, more specifically, by the robotic arm 316) may be precisely positionable in one or more needed and specific positions and orientations.

The robotic arm(s) 316 may comprise one or more sensors that enable the processor 304 (or a processor of the robot 314) to determine a precise pose in space of the robotic arm (as well as any object or element held by or secured to the robotic arm).

In some embodiments, reference markers (e.g., navigation markers) may be placed on the robot 314 (including, e.g., on the robotic arm 316), the imaging device 312, or any other object in the surgical space. The reference markers may be tracked by the navigation system 318, and the results of the tracking may be used by the robot 314 and/or by an operator of the system 300 or any component thereof. In some embodiments, the navigation system 318 can be used to track other components of the system (e.g., imaging device 312) and the system can operate without the use of the robot 314 (e.g., with the surgeon manually manipulating the imaging device 312 and/or one or more surgical tools, based on information and/or instructions generated by the navigation system 318, for example).

The navigation system 318 may provide navigation for a surgeon and/or a surgical robot during an operation. The navigation system 318 may be any now-known or future-developed navigation system, including, for example, the Medtronic StealthStation™ S8 surgical navigation system or any successor thereof. The navigation system 318 may include one or more cameras or other sensor(s) for tracking one or more reference markers, navigated trackers, or other objects within the operating room or other room in which some or all of the system 300 is located. The one or more cameras may be optical cameras, infrared cameras, or other cameras. In some embodiments, the navigation system 318 may comprise one or more electromagnetic sensors. In various embodiments, the navigation system 318 may be used to track a position and orientation (e.g., a pose) of the imaging device 312, the robot 314 and/or robotic arm 316, and/or one or more surgical tools (or, more particularly, to track a pose of a navigated tracker attached, directly or indirectly, in fixed relation to the one or more of the foregoing). The navigation system 318 may include a display for displaying one or more images from an external source (e.g., the computing device 302, imaging device 312, or other source) or for displaying an image and/or video stream from the one or more cameras or other sensors of the navigation system 318. In some embodiments, the system 300 can operate without the use of the navigation system 318. The navigation system 318 may be configured to provide guidance to a surgeon or other user of the system 300 or a component thereof, to the robot 314, or to any other element of the system 300 regarding, for example, a pose of one or more anatomical elements, whether or not a tool is in the proper trajectory, and/or how to move a tool into the proper trajectory to carry out a surgical task according to a preoperative or other surgical plan.

The database 330 may store information that correlates one coordinate system to another (e.g., one or more robotic coordinate systems to a patient coordinate system and/or to a navigation coordinate system). The database 330 may additionally or alternatively store, for example, one or more surgical plans (including, for example, pose information about a target and/or image information about a patient's anatomy at and/or proximate the surgical site, for use by the robot 314, the navigation system 318, and/or a user of the computing device 302 or of the system 300); one or more images useful in connection with a surgery to be completed by or with the assistance of one or more other components of the system 300; and/or any other useful information. The database 330 may be configured to provide any such information to the computing device 302 or to any other device of the system 300 or external to the system 300, whether directly or via the cloud 334. In some embodiments, the database 330 may be or comprise part of a hospital image storage system, such as a picture archiving and communication system (PACS), a health information system (HIS), and/or another system for collecting, storing, managing, and/or transmitting electronic medical records including image data.

The cloud 334 may be or represent the Internet or any other wide area network. The computing device 302 may be connected to the cloud 334 via the communication interface 308, using a wired connection, a wireless connection, or both. In some embodiments, the computing device 302 may communicate with the database 330 and/or an external device (e.g., a computing device) via the cloud 334.

The system 300 or similar systems may be used, for example, to carry out one or more aspects of the method 500 described herein. The system 300 or similar systems may also be used for other purposes.

Figure 4:
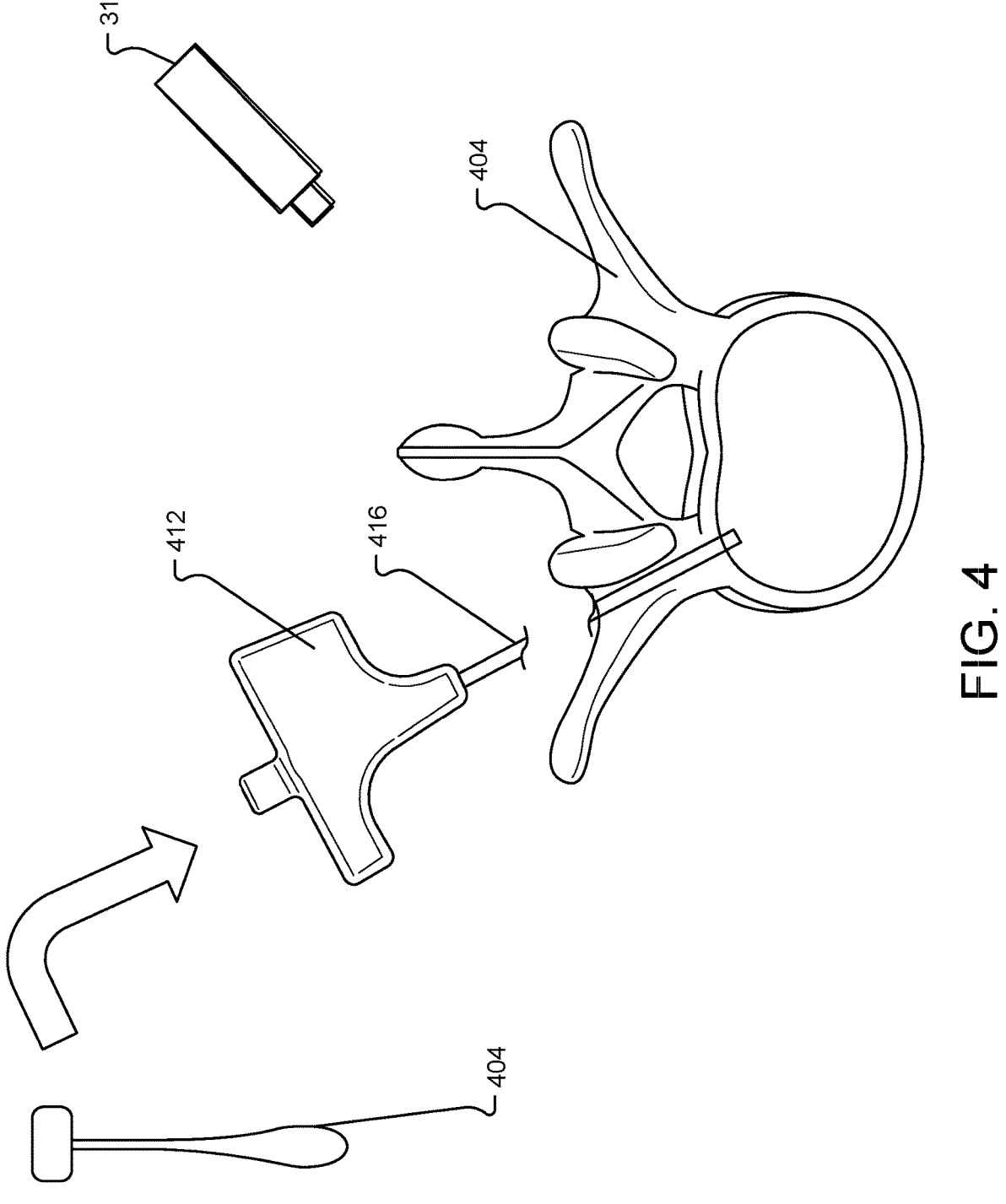
FIG. 4 is a diagram depicting components of a surgical assembly entering an anatomical element according to at least one embodiment of the present disclosure.

FIG. 4 shows an illustrative method of accessing an anatomical element 404 according to at least one embodiment of the present disclosure. As illustrated in FIG. 4, a surgical instrument 408 (e.g., a surgical hammer, a surgical mallet, etc.) may be used by a physician to strike a cannula handle 412, as illustrated by the arrow. By striking the cannula handle 412, the cannula tube 416 may be driven into the anatomical element 404 (e.g., a vertebra) to reach a target surgical site. Once the cannula tube 416 is within the anatomical element 404, a surgical tool (e.g., a surgical tool 102, a surgical tool 202, etc.) may be inserted through the cannula handle 412 and the cannula tube 416 to interact with the target surgical site. For example, the surgical tool may be used to perform an ablation of anatomical tissue found in the surgical site. In one embodiment, the ablation may be performed on the BVN. In some embodiments, the surgeon may use the surgical instrument 408 to strike a strike zone on a proximal end of the surgical tool to guide the ceramic tip to the target surgical site. In some embodiments, imaging devices 312 may be used to capture video, images, or other data associated with the entry of the access tools into the anatomical element 404, which video may be viewed by the surgeon to determine when the access tools have breached the anatomical element 404.

FIG. 5 depicts a method 500 that may be used, for example, to perform an ablation using one or more surgical tools.

The method 500 (and/or one or more steps thereof) may be assisted by, for example, at least one processor. The at least one processor may be the same as or similar to the processor(s) 304 of the computing device 302 described above. The at least one processor may be part of a robot (such as a robot 314) or part of a navigation system (such as a navigation system 318). A processor other than any processor described herein may also be used to assist in the method 500. The at least one processor may execute elements stored in a memory such as the memory 306.

The method 500 comprises accessing a vertebra through the pedicle using a trocar and a cannula assembly using a surgical hammer (step 504). The cannula assembly may include a cannula handle (e.g., a cannula handle 120, a cannula handle 220, etc.) and a cannula tube (e.g., a cannula tube 124, a cannula tube 224, etc.). A surgeon may strike the cannula handle with the surgical hammer to drive the cannula tube into the vertebra. In some embodiments, the surgeon may use data generated by imaging devices (e.g., imaging devices 312) to view the depth and/or angle of the entry of the cannula tube into the vertebra. In some embodiments, the cannula may only be used to breach an outer portion of the vertebra, with other components then used to further enter the vertebra to reach the anatomical site.

The method 500 also comprises removing a straight stylet from the cannula (step 508). Once the surgeon has reached a desired depth, the straight stylet may be removed from the cannula. The straight stylet may be a solid metal portion of the cannula that provides support to the cannula tube as the cannula tube is inserted into the anatomical element. The physician may remove the straight stylet form the cannula through a proximal end of the cannula handle. The removal of the straight stylet may create a hollow passage through the cannula tube to allow for other objects (e.g., a surgical tool) to access the surgical site by passing through the cannula tube.

The method 500 also comprises inserting a J-shaped stylet into the cannula (step 512). The J-shaped stylet (e.g., a J-shaped stylet 156) may be inserted into the cannula tube after the straight stylet is removed from the cannula tube.

The method 500 also comprises striking the J-shaped stylet with the surgical hammer until the target location in the vertebra is reached (step 516). The J-shaped stylet may, when struck by the surgical hammer, create a curved cut through the anatomical element to reach the target surgical site. For instance, the target site may be the BVN of the vertebra. In some embodiments, the J-shaped stylet may be connected to a ceramic tip (e.g., ceramic tip 260) or other surgical tip capable of burrowing through the anatomical tissue of the vertebra to reach the target surgical site (e.g., the BVN). In some embodiments, the surgeon may use data generated by the imaging devices (e.g., imaging devices 312) to view the depth and/or angle of the entry of the J-shaped stylet into the vertebra.

The method 500 also comprises removing the J-shaped stylet from the cannula (step 520). Once the surgical site is reached, the J-shaped stylet may be extracted from the cannula through a proximal end of the cannula handle.

The method 500 also comprises inserting an RF probe into the cannula and advance the RF probe through the channel to the target location (step 524). The RF probe (e.g., surgical tool 102, surgical tool 202, etc.) may be advanced through the tunnel created by the J-shaped stylet until the target surgical site is reached. In some embodiments, the RF probe may be inserted along with the J-shaped stylet (e.g., the J-shaped stylet may be inserted into an interior of the RF probe before the RF probe is inserted into the cannula). The insertion with the J-shaped stylet may provide additional structure to the RF probe, making it easier for the surgeon to insert the RF probe.

The method 500 also comprises turning on a generator to begin an RF treatment (step 528). In some embodiments, the RF treatment may be ablation of the anatomical tissue proximate the surgical site (e.g., the BVN) by passing an RF current through the anatomical tissue. In some embodiments, the ablation may be monitored (e.g., using imaging devices such as imaging devices 312) and/or one or more sensors or thermocouples (e.g., thermocouple 132, thermocouple 232, etc.) coupled with one or more components of the RF probe. In some embodiments, the J-shaped stylet inserted with the RF probe may be removed before beginning ablation.

The method 500 also comprises removing the RF probe from the vertebra once the procedure is complete (step 532).

After ablation, the RF probe may be extracted through the proximal end of the cannula handle. The cannula handle and the cannula tube may also be extracted from the patient.

The present disclosure encompasses embodiments of the method 500 that comprise more or fewer steps than those described above, and/or one or more steps that are different than the steps described above.

As noted above, the present disclosure encompasses methods with fewer than all of the steps identified in FIG. 5 (and the corresponding description of the method 500), as well as methods that include additional steps beyond those identified in FIG. 5 (and the corresponding description of the method 500). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A surgical tool for ablating anatomical tissue, the surgical tool comprising:
   a first cylindrical tube comprising an electrically conductive material;
   a second cylindrical tube comprising an electrically conductive material, wherein the first cylindrical tube is disposed concentrically within an interior of, and is slidable axially with respect to, the second cylindrical tube;
   a distal tip coupled to a distal end of the first cylindrical tube and defining a distal end of the surgical tool opposite a proximal end of the surgical tool, wherein the distal tip is sufficiently shaped or dimensioned to prevent a distal end of the first cylindrical tube from fully sliding into the interior of the second cylindrical tube;

a J-shaped stylet capable of being inserted into an interior of the first cylindrical tube via a directed movement of the J-shaped stylet by a user of the surgical tool; and an elongate core disposed in the interior of the second cylindrical tube and further disposed in at least a proximal portion of the interior of the first cylindrical tube to provide structural support for the first cylindrical tube, wherein a distal end of the elongate core is coupled to a proximal end of the J-shaped stylet, and wherein the J-shaped stylet is configured to be alternately inserted into, and removed from, the interior of the first cylindrical tube via directed movements by the user axially toward, and away from, respectively, the distal end of the surgical tool.

2. The surgical tool of claim 1, further comprising:

a first insulative layer disposed between and electrically isolating the first cylindrical tube and the second cylindrical tube; and a heat shrinkable layer disposed around at least a portion of the second cylindrical tube.

3. The surgical tool of claim 1, wherein the first cylindrical tube being slidable axially with respect to the second cylindrical tube provides a telescoping structure proximate to the distal end of the surgical tool, and wherein the telescoping structure is configured to be:

extended distally outward from a retracted state by the directed movement of the elongate core by the user axially toward the distal end of the surgical tool; and remain in an extended state following the directed movement of the elongate core by the user axially away from the distal end of the surgical tool.

4. The surgical tool of claim 1, wherein the J-shaped stylet, as inserted into the interior of the first cylindrical tube, is configured to be rotated via a directed movement of the elongate core by the user about an axis of the first cylindrical tube to thereby steer the distal tip toward a target ablation location of the surgical tool.

5. The surgical tool of claim 1, wherein at least one of:

at least a portion of the first cylindrical tube proximate to the distal end thereof; and at least a portion of the second cylindrical tube proximate to a distal end thereof, is segmented or braided to provide flexibility or bendability.

6. The surgical tool of claim 2, further comprising:

a cannula handle; and a cannula tube connected to the cannula handle, wherein a portion of at least one of the first cylindrical tube, the second cylindrical tube, and the first insulative layer is positioned in an interior of the cannula tube.

7. The surgical tool of claim 1, wherein the distal tip comprises a hole, and wherein at least a portion of the J-shaped stylet in an inserted state extends through the hole of the distal tip.

8. The surgical tool of claim 1, wherein at least a portion of the distal tip extends radially outward from the distal end of the first cylindrical tube and beyond at least a portion of the circumference of the first cylindrical tube.

9. The surgical tool of claim 1, wherein the first cylindrical tube is configured to be coupled to a Radiofrequency (RF) current source to enable a flow of the RF current to be directed to the anatomical tissue, and wherein the second cylindrical tube is configured to receive a return path of the RF current from the anatomical tissue after at least a portion of the RF current passes through the anatomical tissue.

10. An apparatus, comprising:

a Radiofrequency (RF) probe, the RF probe comprising:

a first cylindrically-shaped electrode extending axially from a proximal end of the RF probe to a distal end of the RF probe;

a second cylindrically-shaped electrode extending axially from the proximal end of the RF probe to a first distance from the distal end of the RF probe, wherein the first cylindrically-shaped electrode is disposed concentrically within an interior of, and is slidable axially with respect to, the second cylindrically-shaped electrode; and a conductive tip electrically coupled with the first cylindrically-shaped electrode at a distal end thereof, wherein the conductive tip is sufficiently shaped or dimensioned to prevent the distal end of the first cylindrically-shaped electrode from fully sliding into the interior of the second cylindrically-shaped electrode;

a J-shaped stylet capable of being inserted into an interior of the first cylindrically-shaped electrode via a directed movement of the J-shaped stylet by a user of the apparatus;

a metal core attached to a proximal end of the J-shaped stylet; and a pull handle attached to a distal end of the metal core, wherein the pull handle, when pulled toward the proximal end of the RF probe, causes the metal core and the J-shaped stylet to slide out of the interior of the first cylindrically-shaped electrode.

11. The apparatus of claim 10, wherein the RF probe further comprises:

a first insulation layer disposed around the first cylindrically-shaped electrode, the first insulation layer electrically isolating the first cylindrically-shaped electrode and the second cylindrically-shaped electrode.

12. The apparatus of claim 10, wherein the first cylindrically-shaped electrode being slidable axially with respect to the second cylindrically-shaped electrode provides a telescoping structure proximate to the distal end of the RF probe, and wherein the telescoping structure is configured to be:

extended distally outward from a retracted state by a directed movement of the metal core by the user axially toward the distal end of the RF probe; and remain in an extended state following a directed movement of the metal core by the user axially away from the distal end of the RF probe.

13. The apparatus of claim 10, wherein the RF probe further comprises:

a heat shrinkable material disposed around at least a portion of the second cylindrically-shaped electrode.

14. The apparatus of claim 10, wherein the RF probe further comprises:

a thermocouple coupled with the conductive tip, the thermocouple configured to generate a reading indicative of a temperature of the conductive tip.

15. The apparatus of, claim 10, further comprising:

a cannula handle; and a cannula tube extending from the cannula handle in a first direction, wherein the RF probe is at least partially contained within the cannula tube.

16. The apparatus of claim 10, wherein at least one of the metal core or the J-shaped stylet comprises Nitinol.

17. The apparatus of claim 13, wherein the heat shrinkable material comprises polyethylene terephthalate, polyether ether ketone, or polyimide.

18. The apparatus of claim 10, wherein the first cylindrically-shaped electrode is configured to be coupled to an RF current source to enable a flow of the RF current to be directed to an anatomical tissue, and wherein the second cylindrically-shaped electrode is configured to receive a return path of the RF current from the anatomical tissue after at least a portion of the RF current passes through the anatomical tissue.

19. An apparatus, comprising:

a cannula handle;

a cannula tube attached to the cannula handle;

a surgical tool capable of passing through an interior of the cannula tube to access an anatomical tissue, the surgical tool comprising:

a tubular proximal electrode;

a tubular distal electrode slidably disposed within an interior of the proximal electrode;

a surgical tip coupled to a distal end of the distal electrode and defining a distal end of the surgical tool opposite a proximal end of the surgical tool, wherein the surgical tip is sufficiently shaped or dimensioned to prevent a distal end of the distal electrode from fully sliding into the interior of the proximal electrode;

a J-shaped stylet capable of being inserted into an interior of the distal electrode via a directed movement of the J-shaped stylet by a user of the apparatus; and a metal core at least partially disposed and further disposed in at least a proximal portion of the interior of the distal electrode to provide structural support for the distal electrode, wherein a distal end of the metal core is coupled to a proximal end of the J-shaped stylet, and wherein the J-shaped stylet is configured to be alternately inserted into, and removed from, the interior of the distal electrode via directed movements by the user axially toward, and away from, respectively, the distal end of the surgical tool.

20. The apparatus of claim 19, wherein the distal electrode being slidably disposed within the interior of the proximal electrode provides a telescoping structure proximate to the distal end of the surgical tool, and wherein the telescoping structure is configured to be:

extended distally outward from a retracted state by the directed movement of the metal core by the user axially toward the distal end of the surgical tool; and remain in an extended state following the directed movement of the metal core by the user axially away from the distal end of the surgical tool.

* * * * *